United States Patent
Jung et al.

(10) Patent No.: US 9,364,071 B2
(45) Date of Patent: Jun. 14, 2016

(54) SYSTEMS AND METHODS FOR MEASURING SPECTRA OF SKIN AND OTHER OBJECTS AND MATERIALS AND MAKING PREDICTIONS BASED THEREON

(71) Applicant: Spectral Sensors Inc., Marshall, TX (US)

(72) Inventors: Wayne D Jung, Morton Grove, IL (US); Russell W. Jung, Morton Grove, IL (US); Walter W Sloan, Lake Bluff, IL (US); Paresh Patel, Morgan Hill, CA (US); Alan R Loudermilk, Marshall, TX (US); Joseph Dale Martens, Chicago, IL (US)

(73) Assignee: SPECTRAL SENSORS INC., Marshall, TX (US)

( * ) Notice: Subject to any disclaimer, the term of this patent is extended or adjusted under 35 U.S.C. 154(b) by 0 days.

(21) Appl. No.: 14/490,666

(22) Filed: Sep. 18, 2014

(65) Prior Publication Data
US 2015/0092191 A1  Apr. 2, 2015

Related U.S. Application Data

(60) Provisional application No. 61/880,157, filed on Sep. 19, 2013.

(51) Int. Cl.
*G01J 3/40* (2006.01)
*A45D 44/00* (2006.01)
(Continued)

(52) U.S. Cl.
CPC ............ *A45D 44/005* (2013.01); *A61B 5/0022* (2013.01); *A61B 5/0075* (2013.01); *A61B 5/1032* (2013.01); *A61B 5/7264* (2013.01); *G01J 3/0254* (2013.01); *G01J 3/0272* (2013.01); *G01J 3/463* (2013.01); *G01J 3/524* (2013.01); *G01N 21/255* (2013.01); *G01J 3/465* (2013.01); *G01J 2003/466* (2013.01); *G01N 2201/062* (2013.01);
(Continued)

(58) Field of Classification Search
CPC . G01J 3/0254; G01J 3/524; G01J 2001/0481; G01N 2201/065; G01N 2201/127
See application file for complete search history.

(56) References Cited

U.S. PATENT DOCUMENTS 4,654,794 A * 3/1987 O'Brien ................. 433/215
5,268,749 A * 12/1993 Weber et al. ............ 356/446
(Continued)

OTHER PUBLICATIONS

K. Grandin "Evaluation of correction factors for transmittance measurements in single-beam integrating spheres", Applied Optics Sep. 1, 1994.*
(Continued)

*Primary Examiner* — Michael A Lyons
*Assistant Examiner* — Maurice Smith
(74) *Attorney, Agent, or Firm* — Loudermilk & Associates

(57) ABSTRACT

Systems and methods for measuring spectra and other optical characteristics such as colors, translucence, gloss, and other characteristics of objects and materials such as skin. Instruments and methods for measuring spectra and other optical characteristics of skin or other translucent or opaque objects utilize an abridged spectrophotometer and improved calibration/normalization methods. Improved linearization methods also are provided, as are improved classifier-based algorithms. User control is provided via a graphical user interface. Product or product formulations to match the measured skin or other object or to transform the skin or other object are provided to lighten, darken, make more uniform and the like.

7 Claims, 33 Drawing Sheets

(51) Int. Cl.
- *G01J 3/02* (2006.01)
- *G01J 3/52* (2006.01)
- *G01N 21/25* (2006.01)
- *A61B 5/00* (2006.01)
- *G01J 3/46* (2006.01)
- *A61B 5/103* (2006.01)

(52) U.S. Cl.
CPC ...... *G01N 2201/08* (2013.01); *G01N 2201/125* (2013.01); *G01N 2201/127* (2013.01)

(56) References Cited

U.S. PATENT DOCUMENTS

| | | | | |
|---|---|---|---|---|
| 5,359,406 A | * | 10/1994 | Suzuki | 356/236 |
| 5,781,342 A | * | 7/1998 | Hannon et al. | 359/599 |
| 5,923,039 A | * | 7/1999 | Jablonski et al. | 250/373 |
| 6,088,117 A | * | 7/2000 | Imura et al. | 356/445 |
| 6,335,792 B1 | * | 1/2002 | Tsuchiya | 356/432 |
| 7,116,420 B2 | * | 10/2006 | Skierski et al. | 356/408 |
| 2007/0201039 A1 | * | 8/2007 | Grygier et al. | 356/521 |
| 2011/0205541 A1 | * | 8/2011 | Osawa et al. | 356/402 |
| 2012/0229801 A1 | * | 9/2012 | Park et al. | 356/236 |

OTHER PUBLICATIONS

J.J Clarke, "Correction Methods for Integrating-Sphere Measurement of Hemispherical Reflectance", National Physical Laboratory 1986.*

* cited by examiner

Table 1. CIELAB ΔE 1994 for Linear Calibration on White

| Measured Reference Standard | CIELAB ΔE 1994 |
|---|---|
| White (Adjusted) | 0.0 |
| 50% Gray | 4.6 |
| 20% Gray | 4.9 |
| Black | 2.8 |

FIG. 5B

Table 2. CIELAB ΔE 1994 for Linear Calibration and the Cavity Model

| Measured Standard | Linear Calibration | Cavity Model |
|---|---|---|
| White | 0.0 | 0.0 |
| 50% Gray | 4.6 | 0.0 |
| 20% Gray | 4.9 | 0.0 |
| Black | 2.8 | 0.0 |
| Red | 3.6 | 0.3 |
| Green | 3.5 | 1.3 |
| Blue | 4.2 | 1.3 |
| Yellow | 2.1 | 1.5 |
| Cyan | 3.2 | 1.4 |
| Orange | 2.3 | 0.7 |
| Purple | 5.5 | 1.4 |
| Violet | 6.0 | 1.9 |

FIG. 5G

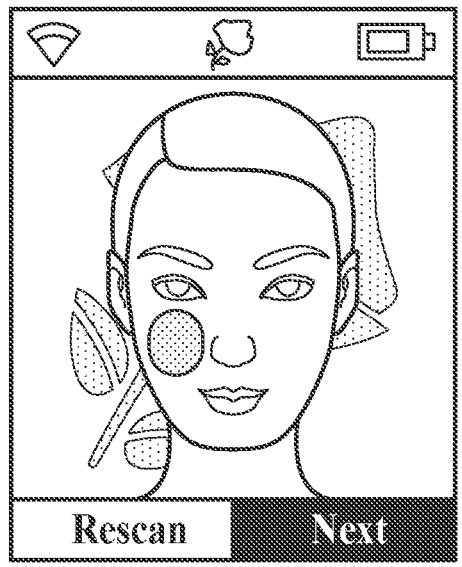
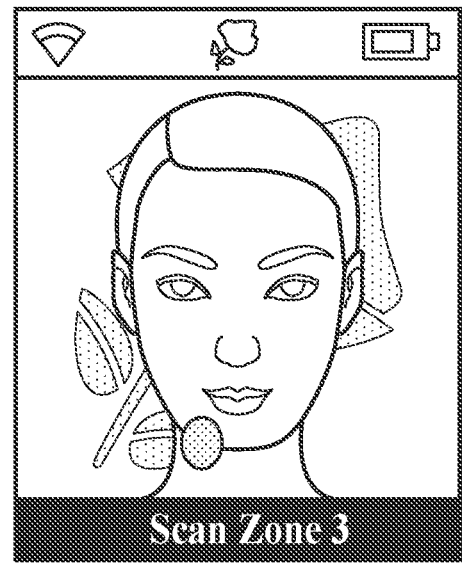
FIG. 7I    FIG. 7J
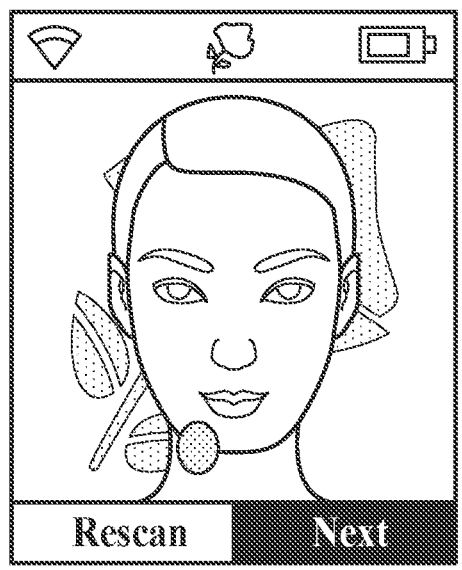
FIG. 7K

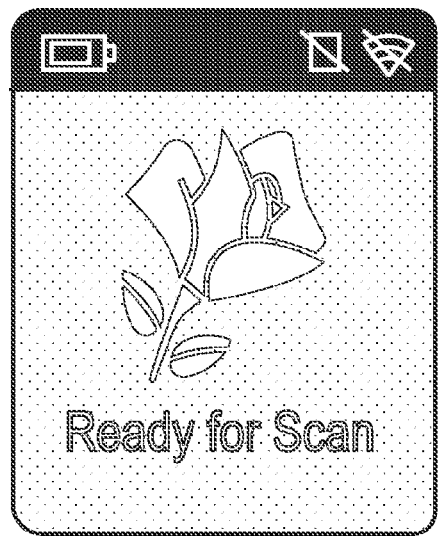
FIG. 7JJ  FIG. 7KK
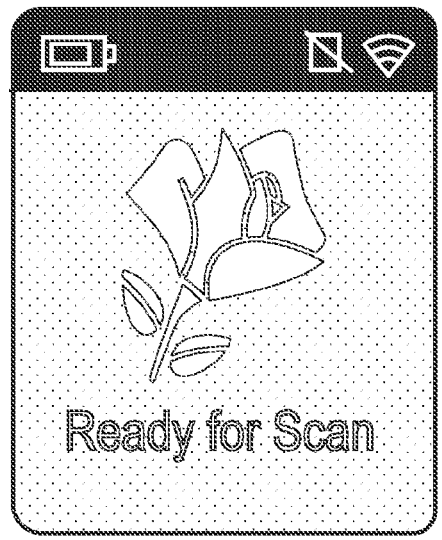
FIG. 7LL  FIG. 7MM

SYSTEMS AND METHODS FOR MEASURING SPECTRA OF SKIN AND OTHER OBJECTS AND MATERIALS AND MAKING PREDICTIONS BASED THEREON

Priority is claimed on Prov. App. No. 61/880,157, filed 2013 Sep. 19.

FIELD OF THE INVENTION

The present invention relates to measuring spectra and other optical characteristics such as colors, translucence, gloss, and other characteristics of objects and materials such as skin, and more particularly to devices and methods for measuring spectra and other optical characteristics of skin or other translucent or opaque objects and for predicting products or product formulations to match the measured skin or other object or to transform the skin or other object in a desired manner (e.g., lighten, darken, make more uniform, etc.).

BACKGROUND OF THE INVENTION

A need has been recognized for devices and methods for measuring spectral, color or other optical characteristics of skin, hair, teeth and other objects, and for predicting or otherwise determining cosmetics (such as foundations), color preparations, restorations or other processes based on such measured optical characteristics. Reference is made to the following applications, which are hereby incorporated by reference, which disclose various systems and methods for measuring various objects and related systems, methods and technologies: U.S. application Ser. No. 09/091,208, filed on Jun. 8, 1998, which is based on International Application No. PCT/US97/00126, filed on Jan. 2, 1997, which is a continuation in part of U.S. application Ser. No. 08/581,851, now U.S. Pat. No. 5,745,229, issued Apr. 28, 1998, for Apparatus and Method for Measuring Optical Characteristics of an Object; U.S. application Ser. No. 09/091,170, filed on Jun. 8, 1998, which is based on International Application No. PCT/US97/00129, filed on Jan. 2, 1997, which is a continuation in part of U.S. application Ser. No. 08/582,054, now U.S. Pat. No. 5,759,030 issued Jun. 2, 1998, for Apparatus and Method for Measuring Optical Characteristics of Teeth; PCT Application No. PCT/US98/13764, filed on Jun. 30, 1998, which is a continuation in part of U.S. application Ser. No. 08/886,223, filed on Jul. 1, 1997, for Apparatus and Method for Measuring Optical Characteristics of an Object; PCT Application No. PCT/US98/13765, filed on Jun. 30, 1998, which is a continuation in part of U.S. application Ser. No. 08/886,564, filed on Jun. 30, 1998, for Apparatus and Method for Measuring Optical Characteristics of Teeth; and U.S. application Ser. No. 08/886,566, filed on Jul. 1, 1997, for Method and Apparatus for Detecting and Preventing Counterfeiting. Reference also is made to PCT App. Ser. No. PCT/US03/05310 filed on 21 Feb. 2003, which is a continuation in part of U.S. application Ser. No. 10/081,879, filed on 21 Feb. 2002, both of which are also hereby incorporated by reference. Reference also is made to U.S. application Ser. No. 11/374,446, filed on Mar. 13, 2005, for System and Method for Preparing Dental Restorations, which also is hereby incorporated by reference. Reference also is made to Provisional U.S. Application Ser. No. 61/852,136, filed Mar. 15, 2013 for Light to Frequency Converter with Electronic Bias and Adjustable Gain, which also is hereby incorporated by reference. The foregoing patent documents are sometimes referenced collectively herein as the "Referenced Patent Documents."

Attempts have been made to measure skin, teeth, hair and other parts of the body with a variety of different implements with varying degrees of acceptability. For example, systems in accordance with the Referenced Patent Documents have been used to measure and shade match teeth in a commercially desirous manner. Other attempts to measure skin have been less successful, and the need remains for systems and methods that measure skin, that process data resulting from such measurements to compute color values and/or predict shade or cosmetic products, and that communicate data resulting from such measurements (or product selection or sales data) to external computing and/or storage resources.

SUMMARY OF THE INVENTION

Based on the Referenced Patent Documents, systems and methods for measuring optical properties are provided that enable, for example, spectral measurements of skin, hair and other parts of the body. Such systems and methods desirably provide spectral measurements with a handheld device enabling a plurality of desired locations to be measured (e.g., forehead, check and neck areas) conveniently and easily, including in retail sales environments. In accordance with preferred embodiments, the handheld device processes data resulting from the spectral measurements to compute color values (e.g., $L^*$, $a^*$, $b^*$ values or $L^*$, $C^*$, $h^*$ values), and based on such data and/or such computed values one or more cosmetic products (e.g., a foundation) may be selected. Such selection preferably is determined based on a prediction algorithm which provides a prediction of a cosmetic product that a human observer would affirm is a good match or otherwise a suitable selection for the skin being measured. In accordance with some preferred embodiments, the prediction algorithm is based on a classifier model that assesses data obtained from clinical studies for selection of the cosmetic products. Preferably, the prediction algorithm adapts based on the collection of additional data of the device as used in the field or commercial setting. Still preferably, the device operates in accordance with a user interface that guides users (e.g., unscientifically trained users) to make spectral measurements and provide product or other predictions in an intuitive and easy-to-use manner. In accordance with preferred embodiments, the device preferably communicates with an external computer network, which may be by wired (e.g., USB) connection but preferably is wireless (WiFi, Bluetooth, etc.). In preferred embodiments, the device communicates wirelessly to an external network and also to a companion device such as a smartphone, tablet, notebook computer or other computing device.

Accordingly, it is an object of the present invention to provide systems and methods for measuring spectral or other optical properties of skin, hair or other parts of the body.

It is another object of the present invention to provide systems and methods for communicating data resulting from such measurements, or predictive or other assessments based on such resulting data, via a display integral to the device to communicating via a wired or preferably wireless data connection to an external network.

It is yet another object of the present invention to provide a classifier model for predicting, e.g., foundations or other cosmetic products that match or desirably correspond to measured skin (or hair products in the case of measured hair, etc.).

It further is an object of the present invention to provide an intuitive and easy to user interface to guide users, including non-scientifically trained users, in the taking of spectral measurements and the output or communication of measurement data or predictive or other data based thereon.

Finally, it is an object of the present invention to provide systems and methods for processing and communicating such data to a remote centralized network (e.g., the "cloud," for storage, further processing, generation of updated tables for future predictions, etc.

BRIEF DESCRIPTION OF THE DRAWINGS

The above objects and other advantages of the present invention will become more apparent by describing in detail the preferred embodiments of the present invention with reference to the attached drawings in which:

FIGS. 5A, 5B, 5C, 5D, 5E, 5F and 5G illustrate principles and aspects of linearization processes utilized in accordance with certain preferred embodiments of the present invention;

FIGS. 7A, 7B, 7C, 7D, 7E, 7F, 7G, 7H, 7I, 7J, 7K, 7L, 7M, 7N, 7O, 7P, 7Q, 7R, 7S, 7T, 7U, 7V, 7W, 7X, 7Y, 7Z, 7AA, 7BB, 7CC, 7DD, 7EE, 7FF, 7GG, 7HH, 7II, 7JJ, 7KK, 7LL, 7MM, 7NN, 7OO, 7PP and 7QQ illustrate exemplary screens displayed utilized in accordance with certain preferred embodiments of the present invention.

DETAILED DESCRIPTION OF THE PREFERRED EMBODIMENTS

The present invention will be described in greater detail with reference to certain preferred and alternative embodiments. As described below, refinements and substitutions of the various embodiments are possible based on the principles and teachings herein.

The Referenced Patent Documents describe a variety of systems and devices for measuring optical properties of skin, hair, teeth and a wide variety of materials and objects, and various methods relating thereto and various systems and methods that advantageously utilize data generated by such systems and devices. Improved systems and methods, and additional inventions and various preferred and alternative embodiments thereof, will be further described herein.

Figure 1:
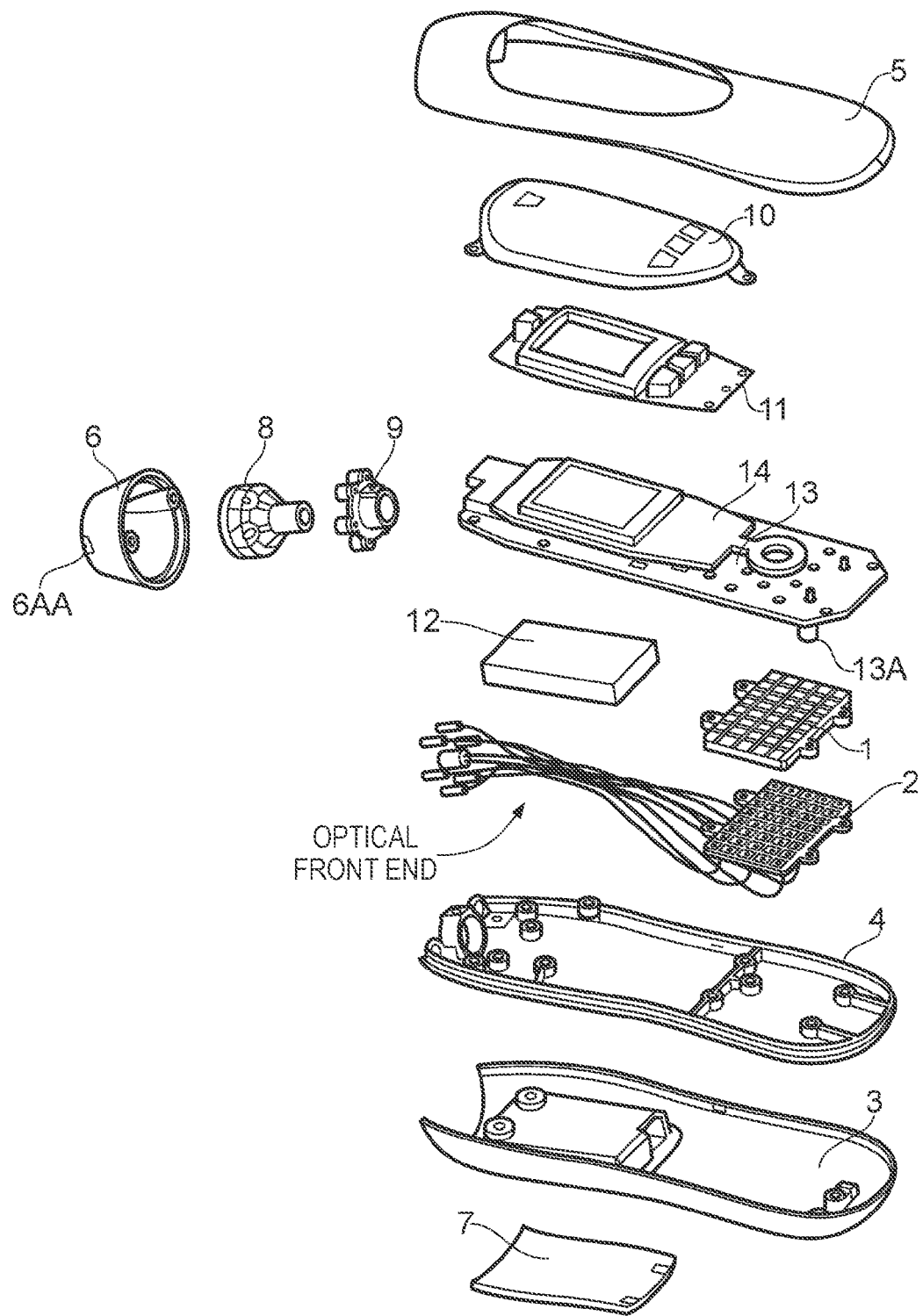
FIGS. 1, 2 and 2A illustrate hardware and physical design aspects of certain preferred embodiments of the present invention.

FIG. 1 illustrates an exploded view of a preferred embodiment of a handheld spectrophotometric instrument. In accordance with such preferred embodiments, the instrument is handheld and generally enclosed by handpiece top 5 and handpiece bottom 3. Preferably clear, transparent or translucent Liquid Crystal Display (LCD) cover 10 provides a substantially sealed window for view of an LCD positioned thereunder. In preferred embodiments, a flexible and preferably polymeric LCD housing/buttons implement 11 is provided to surround the LCD display and enable tactile buttons thereunder to be depressed while maintained as secured and preferably dust and moisture prevention sealed enclosure for the instrument. In preferred embodiments, display Printed Circuit Board (PCB) 14 is mechanically and electrically affixed to Central Processing Unit (CPU) PCB 13 as illustrated, although in alternative embodiments electronics of the instrument are included on a single PCB or more than two PCBs. What is important is that electronics are provided in the instrument in order to provide functions and operations as more fully described elsewhere herein.

In preferred embodiments, a 10 nm visible band spectrometer is provided for providing precise spectral measurements, although in other embodiments other spectral resolutions are provided. In accordance with the illustrated embodiment, an optical front end is provided that preferably consists of a center sensor bundle having a terminating end preferably consisting of a metal ferrule positioned in Light Emitting Diode (LED) dome 8. LED dome 8 preferably is a white or near white material such as plastic that provides an optical cavity into which light from a plurality of LEDs is provided. LED dome 8 preferably includes openings into which LEDs are positioned, which are selectively activated under control of a processor included in or on CPU PCB 13. Also in preferred embodiments, the optical front end includes a plurality of LED tracking fiber bundles, which preferably are held by LED tracking array 9, which fits in a substantially co-axial arrangement with LED dome 8. Handpiece tip 6 fits with handpiece top 5 and handpiece bottom 3 to substantially enclose the internal components as illustrated.

Also as illustrated in FIG. 1, other internal components preferably include battery 12, battery cover 7, and handpiece spine 4. Handpiece spine advantageously provides internal structure to the instrument and in addition eases assembly of the internal components. In preferred embodiments, the spectrometer includes up to forty channels, which as described in the Referenced Patent Documents may include optical sensors mounted on CPU PCB 13, which are surrounded by walls of preferably polymeric array fixture 1, which includes cavities or other openings into which preferably bandpass interference filters are positioned. Fiber bundle manifold 2 is coupled preferably to a main sensor fiber bundle and preferably LED tracking fiber bundles. The main sensor fiber bundle preferably includes a probe end extending into a cavity defined by dome 8 and cap 6, and receives light during a measurement into a randomized fiber bundle which is split into a plurality of smaller bundles. Terminating ends of the main sensor and LED tracking fiber bundles are affixed into fiber bundle manifold as illustrated. Reference is made to the Referenced Patent Documents for a discussion of an optical front including a randomized fiber bundle. In accordance with preferred embodiments of the present invention, however, the main sensor bundle and preferably the LED tracking fiber bundle are coated with a black absorbing material. In preferred embodiments, the black materials coating the fiber bundles consists of a silicon rubber based material that is coated (spray or otherwise) onto the fiber bundles. Such black coating serves to protect the fiber bundles and absorb stray light that may result from leakage into the unit or from broken fibers, etc. As will be appreciated by those of skill in the art, the components illustrated in FIG. 1 include details enabling the assembly to be secured such as with screws so that fiber bundle manifold 2, array fixture with filters 1 and CPU PCB are affixed in an appropriate manner. For purposes of explanation additional details such as cabling between CPU PCB 13 and display PCB 14, and connecting wires for powering LEDs that illuminate LED dome 8 are not show, but will be understood by those of skill in the art.

Figure 2:
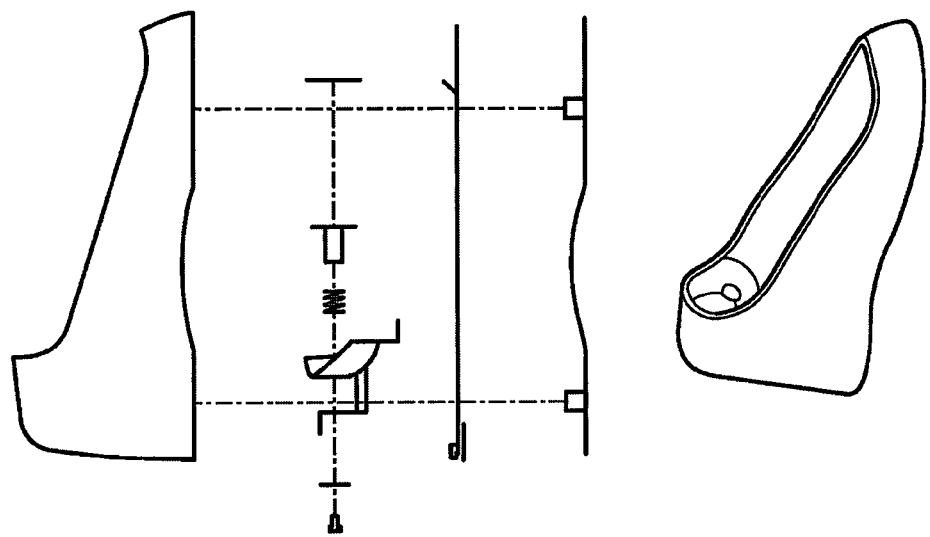
Figure 2:
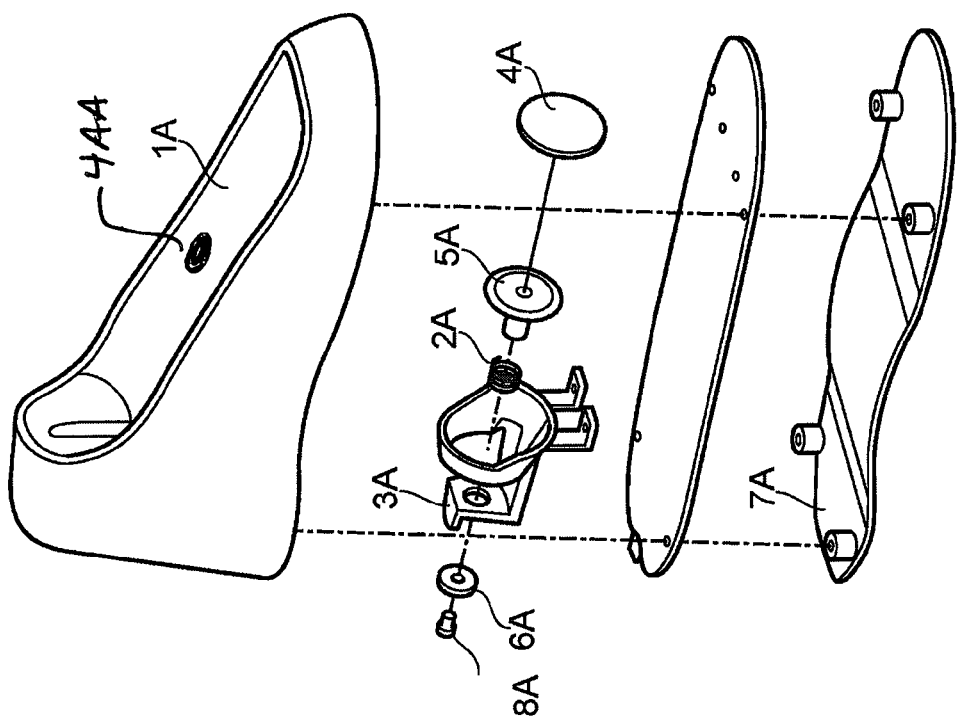

Also as illustrated in FIG. 1, CPU PCB 13 preferably has charging blades or pins 13A which preferably extend through handpiece bottom 3 for electrical engagements with corresponding pins of a charging circuit in a corresponding base unit (see FIG. 2). Also shown in FIG. 1 are magnets 6AA, which preferably are three in number and arranged in and as part of handpiece tip 6. As more fully explained in connection with FIG. 2, magnets 6AA help to bring the end portion of handpiece tip 6 with the surface of an optical reference (see calibration disk 4A of FIG. 2), which in preferred embodiments is used to normalize the instrument prior to at least certain measurements (see also the Referenced Patent Documents for additional details regarding such normalization procedures used in certain embodiments of the present invention). Calibration disk 4A may be, for example, a white or light optical reference.

Referring to FIG. 2, an exploded view of an exemplary base unit is illustrated, which in preferred embodiments is used to desirably provide a normalization reference implement and a charging system for the instrument. The exemplary base unit including main body 1A, bottom cover 7A, charging board with charging blades or pins that electrically engage charging blades 13A of FIG. 1. A source of electrical power, such as from a transformer, DC power supply, etc., not shown and external to the base unit, provides electrical power to the base unit and provides current for charging the handpiece of the instrument. Main body 1A may optionally include a second optical reference 4AA, which, for example, may be a black or dark colored optical reference. Such a second optical reference desirably is positioned so that handpiece tip 6 can be brought into proximity of second optical reference 4AA so that a second calibration or normalization reference may be made.

As discussed elsewhere herein and in the Referenced Patent Documents, in certain preferred embodiments a calibration or normalization reference is brought into proximity of handpiece tip 6 (see FIG. 1) prior to use of the instrument to measure spectrums. Such a normalization process may desirably accommodate changes in the light output from the LEDs and/or other changes in the optical properties of the measurement system. For precise spectral measurements, it is important that handpiece tip 6 be reliably positioned flush with the calibration or normalization reference. Preferred embodiments provide improved implements and methods for such normalization.

In preferred embodiments, the base unit includes probe receptacle 3A, retaining disk 6A, mounting screw 8A, spring 2A and plunger 5A. These elements, and the other elements shown in FIG. 2, provide s movable base for calibration disk 4A, which move to accommodate positioning of handpiece tip 6 inside the base unit and reliably bring handpiece tip 6 into a substantially centered and flush position relative to calibration disk 4A. Also in certain preferred embodiments, calibration disk 4A consists of a white or substantially white coating, such as a fired porcelain or ceramic material, on a metallic substrate. Preferably, the metallic substrate includes or consists of a ferromagnetic material (e.g., steel). In the preferred embodiment, a ceramic material is powder coated and fired to produce a highly inert and durable surface, which is optically stable and may be cleaned. Preferably, an arrangement of magnets 6AA in handpiece tip 6, desirably three magnets in a triangular configuration, are attracted to the magnetic substrate of calibration disk 4A. Thus, in response to a user positioning the handpiece into the base unit, handpiece tip 6 is brought into a flush position relative to calibration disk 4A. Concurrently, charging blades 13A of the handpiece are brought into electrical contact with charging blades of the base unit.

Figure 2A:
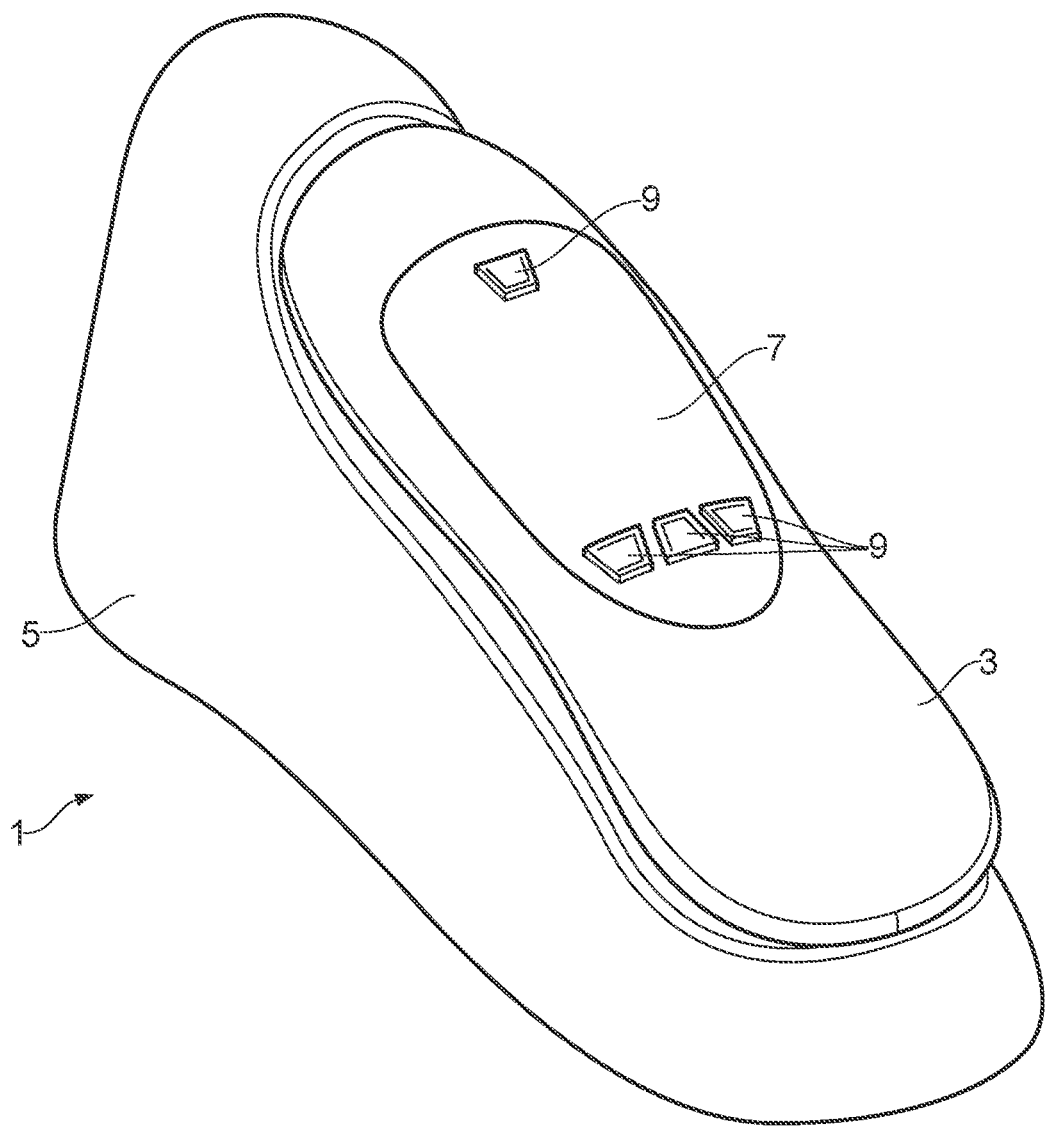

FIG. 2A illustrates an overall view of a preferred embodiment of spectrophotometer system 1 that may be desirably applied to measuring skin, hair and other parts of the human body. Handpiece 3 rests in base unit 5, which generally conforms to the shape of handpiece 3 so that charging contacts of handpiece 3 are brought into electrical contact with corresponding charging contacts in base unit 5. Additionally, the tip of handpiece 3, by the shape of base unit 5 (which may be aided by magnetic-assisted positioning as described elsewhere herein) is brought into a reliable, flush position with a normalization reference included in base unit 5 (all as described in greater detail elsewhere herein). As illustrated, handpiece 3 preferably includes display 7, which buttons 9 preferably positioned in an upper proximate position and in a lower proximate position. While other arrangements of buttons 9 are used in alternative embodiments, in the illustrated embodiment upper button 9 may desirably provide a power on/off (e.g., depress for a predetermined first time interval, such as 2 seconds, to turn on the device, and when in the on state depress for a predetermined second interval of time, such as 5 or 10 seconds, to turn off the device), which also may be used as an activate (e.g., take a measurement) function. Right, left and center lower buttons 9 may be used, for example, to provide a right/left scroll type function, with center lower button 9 providing, for example, a select function. As described elsewhere herein, information displayed on display 7 proximate to particular ones of buttons 9 can indicate to the user the function of the particular button at the point state of operation of the device. In preferred embodiments, different operation modes enable buttons 9 to indicate different functions to the user, and in still other preferred embodiments, the operation of buttons 9 and display 7 may operate in different manners in different points in time based on the contents of Field Programmable Gate Array (FPGA) code utilized in such preferred embodiments.

In accordance with preferred embodiments, the physical shape of the spectrophotometer has a curved overall shape along the length-wise direction such that the planar surface of the tip of the handpiece in which the opening is presented to the portion of the skin being measured is substantially perpendicular to the length-wise direction. The physical shape is arranged so that just the tip of the handpiece is in contact with the portion of the skin being measured.

Figure 3:
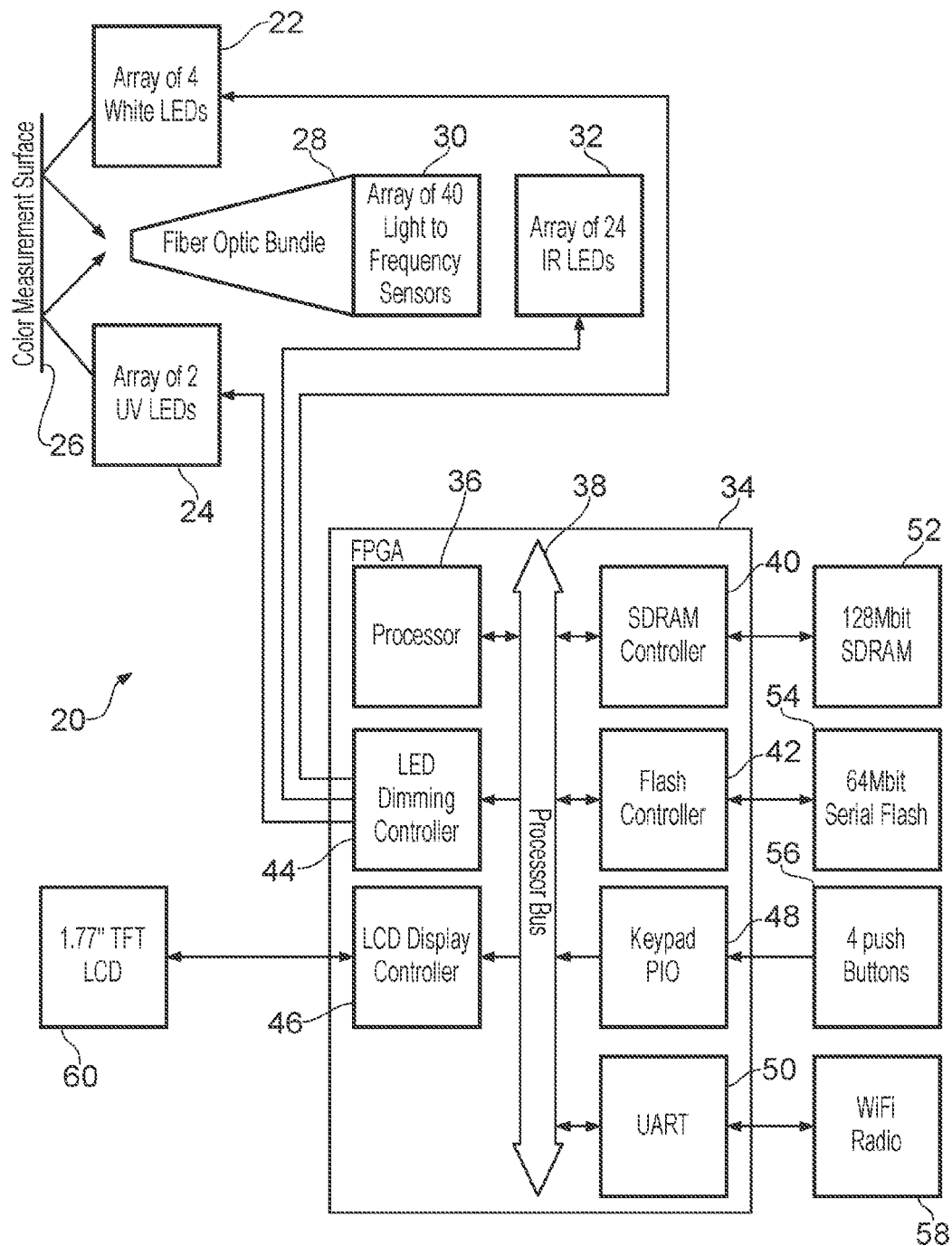
FIG. 3 is a block diagram illustrating electronic components and/or circuit functions of certain preferred embodiments of the present invention.

Referring now to FIG. 3, exemplary electronics included in certain preferred embodiments will now be described.

As described in the Referenced Patent Documents and elsewhere herein, systems and methods in accordance with certain preferred embodiments of the present invention controllably provide light to a surface or material that is to be optically characterized, which may be skin, hair, teeth, paint, ink, fabric, food, plants, gems, etc. such as described in the Referenced Patent Documents, and sense the light returned from the surface material preferably with a plurality of sensors. Preferably, the light source is a broadband light source, such as white LEDs and bulbs of a suitable type (see, e.g., the Referenced Patent Documents). The plurality of sensors preferably include within the sensor light to frequency converters (LFCs) (which may include additional circuitry such as counters and control circuitry so as to output digital values), which receive light after passing through bandpass filters, which preferably consist of interference filters. The use of LFCs, and the use of bandpass/interference filters to separate received light into spectral bands that cover the region of interest, are described in greater detail in the Referenced Patent Documents.

As illustrated in FIG. 3, illumination is provided in the exemplary preferred embodiment by LEDs 22 and 24. While other sources of illumination are within the scope of the present invention, LEDs 22 are commercially available white LEDs. As such LEDs typically provide much lower intensity in the shorter wavelengths, in preferred embodiments violet or ultraviolet (UV) LEDs 24 are optionally provided to increase the illumination intensity in the shorter wavelengths. LEDs 22 and 24 are controlled by FPGA 34, and in particular are controlled by circuitry within FPGA 34 that is logically configured to provide LED dimming controller 44. As will be appreciated by those of skill in the art, LEDs 22 and 24 are controlled to provide illumination of the desired intensity, and the desired duration, to the surface or material to be measured (skin, etc., as denoted by measurement surface 26 in FIG. 3), under control of dimming controller 44.

Based on the characteristics of surface 26, light is received by fiber optic bundle 28 (see also the main sensor bundle of FIG. 1), schematically illustrated in FIG. 3 as a trapezoid but should be understood as bundle of fiber optics. Fiber optic bundle 28 provides a receiver within the optical cavity provided in preferred embodiments, and preferably provides a plurality of outputs that serve to couple light to individual sensors of LFC sensor array 30 via interference filters. While the illustrated embodiment includes 40 individual LFC sensors, in the preferred embodiment 30 of the 40 "channels" are coupled to legs of fiber optic bundle 28, with the respective individual filters being on approximately 10 nm centers from, for example, 410 to 700 nm. In the exemplary preferred embodiment, 7 of the remaining 10 channels are used to monitor or track the illumination provided by LEDs 22 and 24, and enabling the spectrum and overall intensity of the illumination to be tracked by processor 36 and software operating thereon. Such multi-channel tracking and monitoring of the illumination allows processor 36 and software to detect illumination drift, and either alerting the operation to re-normalize the instrument, and or in certain embodiments compensate the measurement in view of the illumination drift.

As explained in the Referenced Patent Documents, in preferred embodiments light bias is provided to some or all of the LFC sensors in order to ensure that each sensor is outputting a count at a desired minimum level. In the embodiment illustrated in FIG. 3, bias illumination is controllably provided, under software control via processor 36 and LED dimming controller 44, through infrared (IR) LEDs 32. As will be understood from FIG. 3, IR LEDs may be selectively stepped to increase their output through pulse width modulation so that the desired sensors of LFC array 40 (which may, for example, be only the sensors used for spectral measurements) output pulses at a desired minimum level. In one preferred embodiment, the amount of bias provided by IR LEDs 32 is increased by a predetermined amount, and the sensors measured to determine if the minimum level is achieved, and if not the amount of bias is increased in a stepwise fashion until it is determined that the minimum level is achieved for the desired LFC sensors. In this fashion, a desirable bias level may be achieved in an automatic fashion. In certain preferred embodiments, this automatic bias setting operation is conducted upon instrument startup, and in other embodiments as part of the normalization process before each use. Also, it should be understood that the use of IR LEDs is exemplary, and other illumination sources, such as a halogen or other incandescent type bulb, which desirably is positioned on the backside of CPU PCB (FIG. 1) and provides illumination that may be received by the LFC sensors, for examples, by holes positioned in the PCB underneath the LFC sensors. Such alternative methods of providing bias illumination are within the scope of the present invention.

Also as illustrated in FIG. 3, preferably implemented in FPGA 34 preferably includes other elements of a computing system for control of the instrument, including, for example, SDRAM controller 40 (to which may be coupled SDRAM 52), Flash controller 42 (to which may be coupled Flash memory 54, which may be, for example a serial Flash memory), keypad peripheral IO (to which may be coupled push buttons 56, which may be of any desired number such as two, three, four, etc., and which may be capacitive or other types of switches known in the art, but which preferably provide tactile feedback to the user), UART 50 for data communications to external devices (to which may be coupled a wireless module such as WiFi radio 58, but which could also be Bluetooth or other standard or custom wired or wireless communication protocols), and LCD displayer controller 46 (to which may be coupled LCD 60 or other suitable display device). Other embodiments include data communication modules such USB (2.0, 3.0, 1.1, etc.). What is important is that FPGA, which preferably is an Altera Cyclone III FPGA as an example, be configured to include the desired circuit functions for the instrument. While other embodiments include individual circuits such as a CPU, memory controllers, display controller, etc., in preferred embodiments FPGA 34 is used and enables the hardware of the instrument to be readily reconfigured for different applications, updated cosmetic/prediction tables and data, adding product lines to the cosmetic/prediction tables, etc.

Figure 4A:
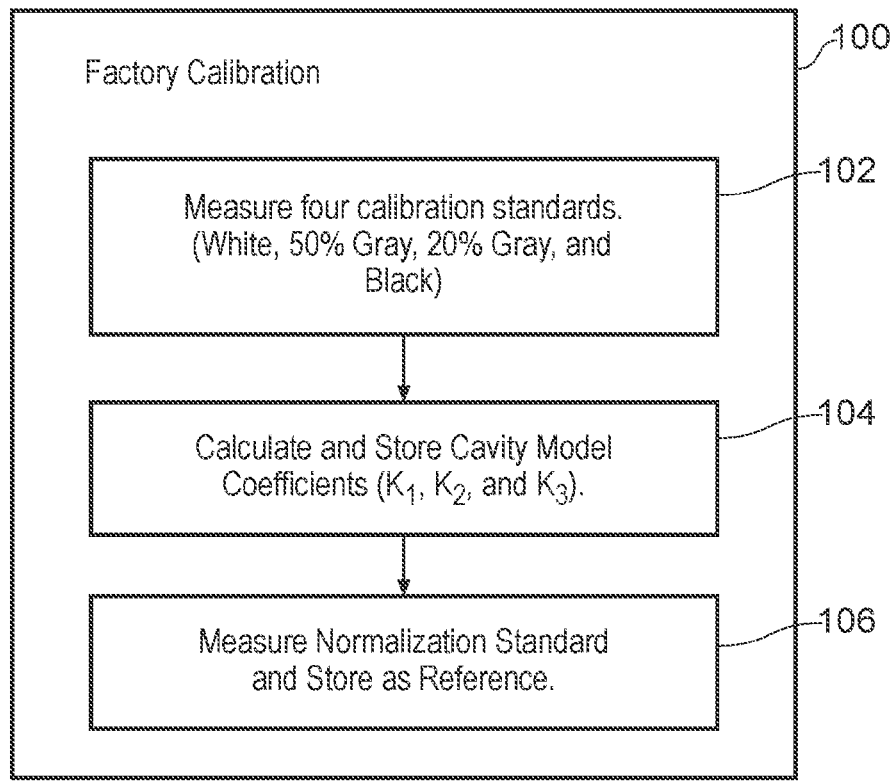
FIGS. 4A, 4B and 4C illustrate exemplary calibration, normalization and measurement methods in accordance with certain preferred embodiments of the present invention.
Figure 4B:
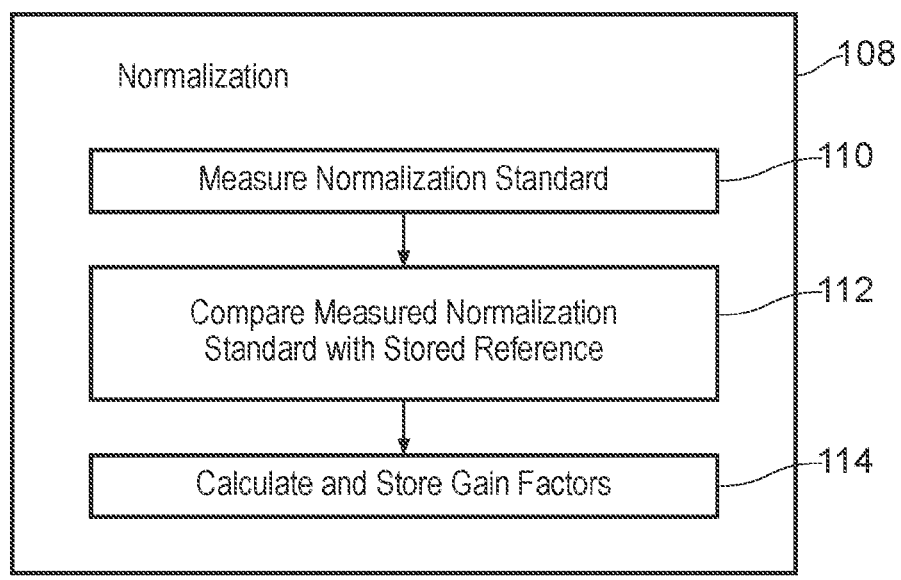
Figure 4C:
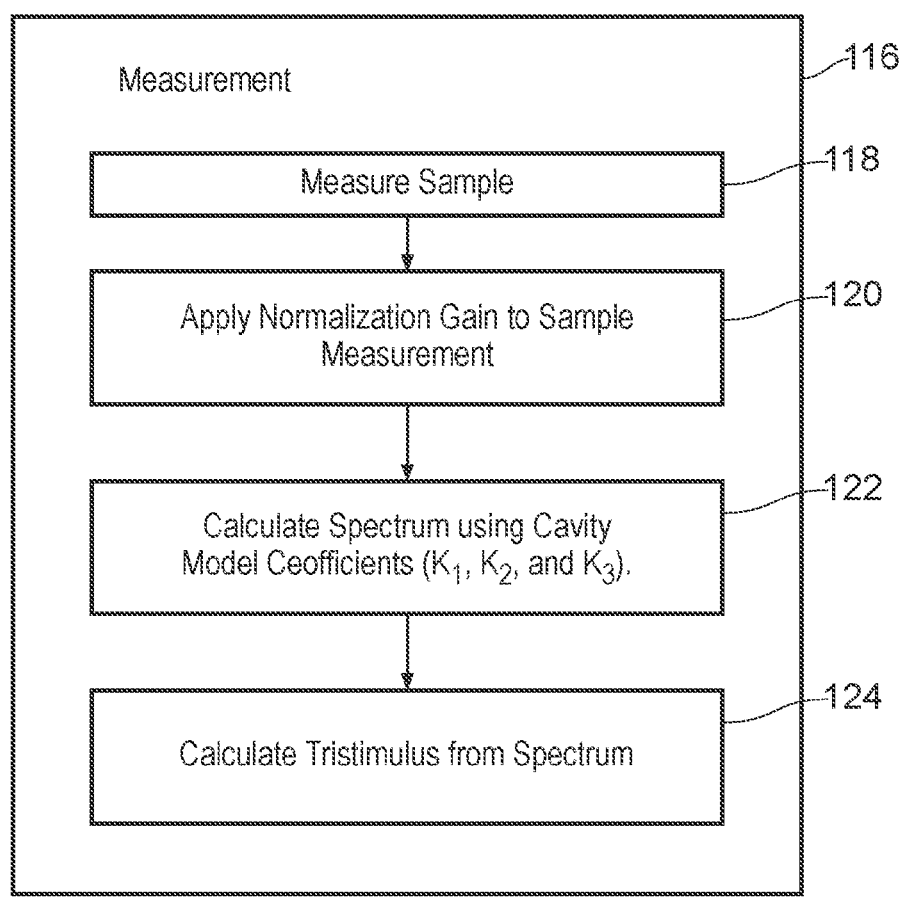

Referring now to FIGS. 4A through 4C, exemplary device operations will now be further described.

Operation 100 of FIG. 4A illustrates an exemplary "factory calibration" operation used in preferred embodiments of the present invention. As illustrated in step 102, an individual instrument measures a plurality of calibration standards, preferably at least four in number. As examples of such calibration standards (e.g., diffuse reflectance standards), refer to the FIGS. 5A through 5G and related description. The results of such measurements are stored for further processing. As illustrated in step 104, coefficients for linearizing spectral bands are calculated based on the stored data from the measurements in step 102 and stored. Such coefficients in preferred embodiments are Cavity Model coefficients as described in greater detail in connection with FIGS. 5A through 5G. As illustrated in step 106, a calibration/normalization standard (i.e., an optical calibration disk such as disk 4A of FIG. 2), which will accompany the instrument and be used to calibrate or normalize the instrument as described elsewhere herein, is measured and the results stored. Optionally at step 106, a second, preferably black, optical reference may be measured, with the results also stored. As will be understood from description elsewhere herein, within the device are stored the preferred Cavity Model coefficients, and the reflectance spectrum of the calibration/normalization reference standard or standards that accompanies the instrument. Generation and storage of such data is used in factory calibration in accordance with preferred embodiments. Also, in accordance with preferred embodiments, handpieces and base units (see FIGS. 1, 2 and 2A) are serialized (e.g., have serial numbers for the handpiece that matches or other corresponds to the particular base unit with which it was factory calibrated).

Operation 108 of FIG. 4B illustrates a normalization/calibration operation that is used in preferred embodiments of the present invention. A calibration/normalization reference standard that is measured during factory calibration is positioned in base unit 5 (see calibration disk 4A of FIG. 2). Prior to making measurements, a calibration/normalization operation is performed (see description elsewhere herein, including FIG. 7B and related description) using the same calibration/normalization reference that was used during factory calibration (step 110), and the results from this calibration/normalization measurement are compared with the stored spectral data of the same calibration/normalization reference (step 112). Based on this comparison, gain factors or coefficients are calculated and stored in the instrument (step 114) and used for subsequent measurements with the instrument (until its next calibration/normalization). Such calibration/normalization tends to compensate for changes in the optical performance of the instrument since its factory calibration, including changes in the light source illumination, changes in the optical properties of the cavity, fiber bundles, filters, etc. Optionally, at step 110, a second, preferably black, reference standard may be measured and data from the first and second normalization reference standard measurements may be used in steps 112 and 114 to calculate the gain factors.

Operation 116 of FIG. 4C illustrates a measurement operation that is used in preferred embodiments of the present invention. At step 118, the sample is measured, which may be skin, hair, or other objects or materials as referenced elsewhere herein or in the Referenced Patent Documents. At step 120, the normalization gain factors/coefficients are applied to the spectral data from the measurement at step 118 to produce a normalized spectrum. At step 122, the normalized spectral data from step 120 are adjusted using linearization coefficients, which in the preferred embodiments are Cavity Model coefficients (see discussion elsewhere herein, including FIGS. 5A to 5G and related description). Step 122 results generally in a normalized, linearized spectrum. Based thereon, at step 124 tristimulus values are calculated. Such values may be used for prediction and selection algorithms, such as described elsewhere herein. Prediction and selection based on spectral data without step 124 also are within the scope of the present invention.

In accordance with preferred embodiments, an optical cavity is presented to the skin or other object or materials under evaluation. The optical cavity receives and reflects preferably broadband light from the illumination source, in preferred embodiments one or a plurality of types of LEDs, with each type of LEDs of one or a plurality of LEDs per type. An opening in the optical cavity allows light to be incident on the surface under evaluation. A portion of this light is received by a receiver, which preferably is a receiver fiber bundle that propagates and couples light to the sensor array via bandpass filters, as described in greater detail elsewhere herein and in the Referenced Patent Documents.

A portion of the light returned from the surface under evaluation, however is not directly received by the receiver/sensor bundle, but instead is incident upon a portion of the optical cavity, and which may reflect this light one or more times such that it is re-incident on the surface under evaluation. Herein, this optical effect is referred to as sample substitute error, sample absorption error, etc. Preferred embodiments of the present invention implement a correction for this error/optical effect, as will be described in connection with FIG. 5A, et seq.

A mathematical model for quantifying single-beam sample absorption error in a preferably hemispherical 45°/0° measurement cavity has been derived and tested by measuring diffuse reflectance standards with a visible-range spectrophotometer in accordance with the present invention. In preferred embodiments, this methodology uses this three-parameter model to correct for sample absorption error, which may be applicable to embodiments of single-beam spectrophotometers described herein and in the Referenced Patent Documents and also in other types of single beam spectrophotometers.

To measure a test sample accurately using a single beam spectrophotometer, the instrument in general should be calibrated using one or more reference standards, and the illumination source should remain unchanged between measurements of the standard and the sample. However, in a finite non-absorptive measurement cavity, such as those found in hand-held spectrophotometers, light reflects off the measurement target, fills the cavity, and falls back onto the measurement target. As a result, the incident flux received by a test sample also is a function of the spectral diffuse reflectance of the test sample, and will be different from the incident flux received by the reference standard(s) during calibration. For samples having lower reflectance than the reference standard used for calibration, this single-beam sample absorption error (see F. J. J. Clarke and J. Anne Compton, "Correction Methods for Integrating-Sphere Measurement of Hemispherical Reflectance," Color Research and Application, 11 (4), (Winter 1986)) (also referred to as "substitution error") results in a downward shift of the measured spectrum.

This problem of sample absorption error does not occur when using a dual-beam spectrophotometer, which simultaneously measures the spectral reflectance of a reference standard and a test sample, and uses the difference between the measured and expected spectra for the reference standard to adjust the measured spectrum of the test sample.

The magnitude of sample absorption error in a single beam spectrophotometer may be reduced by increasing the size of the measurement cavity relative to the size of the sample port (see Ross McCluney, "Ratio of Port Size to Integrating Sphere Diameter," background paper for the National Fenestration Rating Council (Nov. 3, 2006)). However, this solution is problematic for portable instruments. In general, it is impractical to incorporate a large integrating sphere into a portable, hand-held spectrophotometer. Another way to account for sample absorption error is to create a look-up table to provide corrections as a function of measured spectral reflectance for a range of wavelengths (see Labsphere Inc., "Quantitation of Single Beam Substitution Correction in Reflectance Spectroscopy Accessories," Application Note No. 01 (Oct. 5, 2000)). However, such a look-up table in general will only be accurate for the measurement geometry from which the table was derived.

In accordance with certain preferred embodiments, a methodology is provided that may correct for sample absorption error in general in any single-beam spectrophotometer.

Figure 5A:
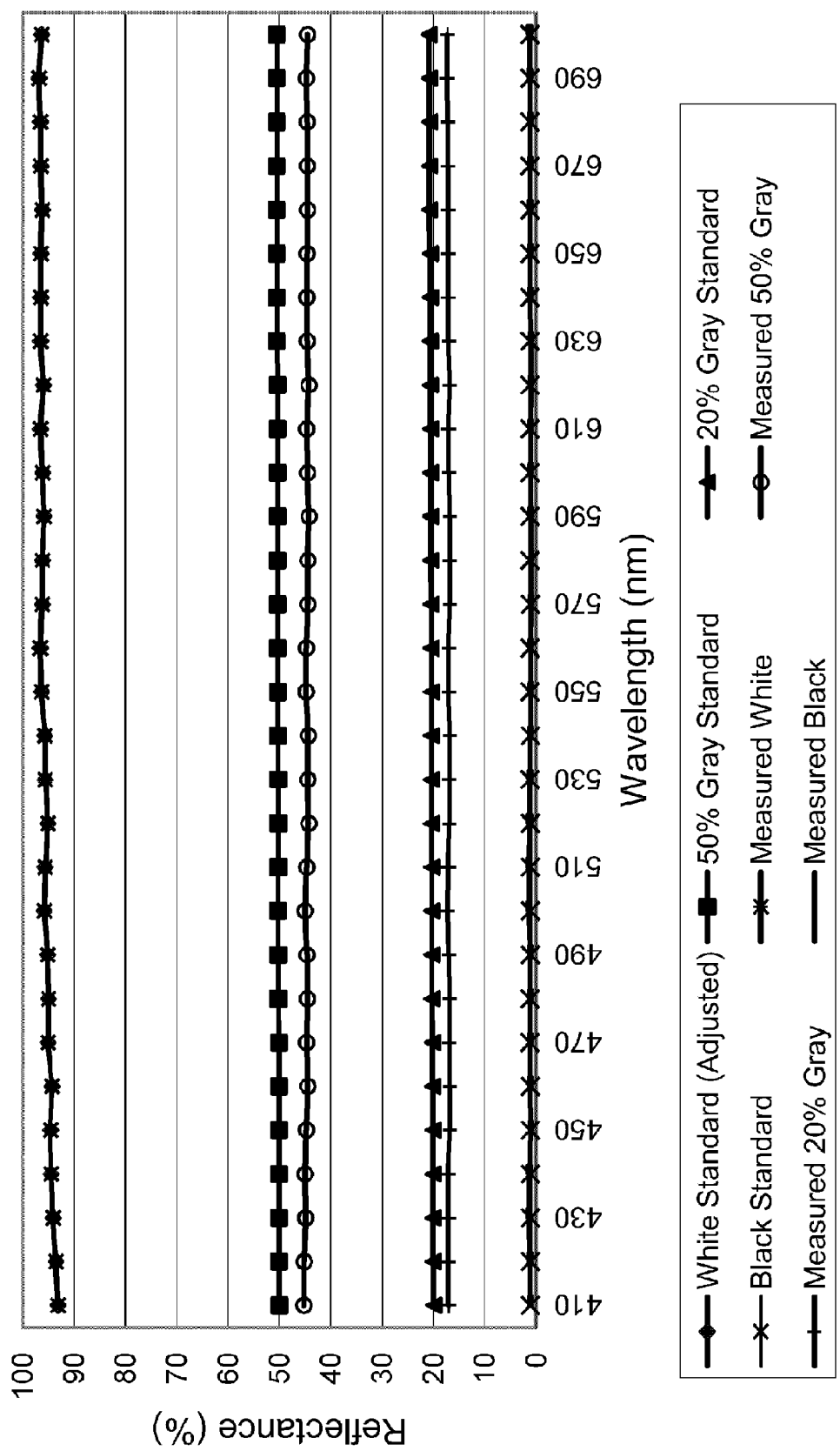

FIG. 5A shows the result of measuring four Labsphere Spectralon® diffuse reflectance standards with a hand-held spectrophotometer in accordance with the present invention. The standards are referred to as White, 50% Gray, 20% Gray, and Black (nominally 2% gray). Each 2" diameter standard is supplied with diffuse reflectance data in the range 250-2500 nm, measured to N.I.S.T. standards using a dual-beam integrating sphere (see Labsphere, Inc., Spectralon® Diffuse Reflectance Standards, http://www.labsphere.com/uploads/datasheets/diffuse-reflectance-standards-product-sheet.pdf). According to Labsphere, the port size for calibration is 25.4 mm.

The hand-held spectrophotometer was configured as follows:

30 sensors (10 nm bandwidth) covering the range 410-700 nm.

Nominal 30 mm diameter white hemispherical measurement cavity.

9 mm diameter measurement aperture.

Six white LEDs in a nominal 45°/0° geometry.

For the data of FIG. 5A, the instrument was linearly calibrated using the White standard. After subtracting the sensor readings for measurement of perfect black (simulated by aiming the instrument toward a distant diffuse black surface), the gains for the sensor readings for measured White were calculated so that the measured spectrum of the White standard agreed with the spectral data provided with the reference standards. Those gains were then used to calculate spectra for measurement of the Gray and Black standards. For the 9 mm aperture of the test instrument, the Labsphere-supplied spectrum for the White standard was adjusted downward by a wavelength-dependent nominal 3.2% to account for edge loss (see Atkins, J. T., and Billmeyer, F. W., "Edge-loss errors in reflectance and transmittance measurement of translucent materials," Materials Research and Standards, 6, (1966)). The methodology for this adjustment will be described later herein. No spectral adjustment was utilized for the opaque Gray and Black standards.

FIG. 5A shows complete spectral agreement for the White standard, which is to be expected, since it was used for calibration. However, the 50% and 20% Gray, and the Black standards are measured too low. This is because when these samples are measured, there is less light reflected back into the cavity and onto the samples than when measuring the white standard that was used for calibration of the instrument. This illustrates sample absorption error. Table 1 (FIG. 5B) shows the color differences, based on CIELAB $\Delta E$ 1994, between the measured spectra of the reflectance standards (with the White standard adjusted for edge loss), and the spectra supplied with each reflectance standard. $L^*a^*b^*$ was calculated using a D50 illuminant and a 2° observer.

Figure 5C:
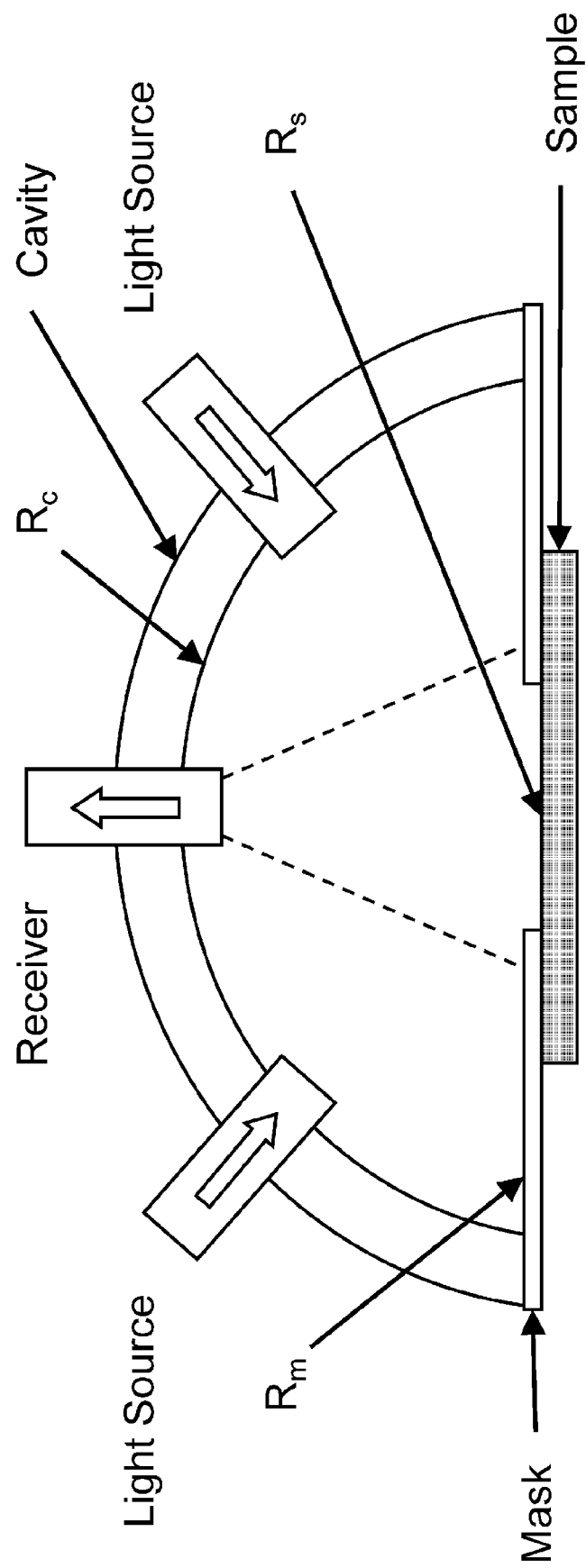

Consider the measurement cavity illustrated in FIG. 5C, which is the general shape of the cavity of the instrument (in accordance with the present invention) used in this test. The measurement cavity preferably has multiple light sources and a fiber-optic receiver. The spectral reflectance of the sample, cavity, and aperture mask are $R_s$, $R_c$, and $R_m$ respectively. Incident flux from the light source strikes the sample and mask, reflects upward to the cavity, then back downward to the sample and mask, reflecting back and forth until extinction. There will be rays that reflect directly between cavity surfaces, but in the configuration of FIG. 5C, it is assumed that these rays will be outside of the numerical aperture of the fiber-optic receiver and can be disregarded.

Let $\Phi$ be the incident flux striking the sample and mask surfaces. The flux reflected from the sample and mask surfaces is a linear function of spectral reflectance of those surfaces. Let factors a and b represent the respective fractions of flux from the sample and mask surfaces that are reflected to the cavity wall and not lost to geometry, edge loss, and other factors. The first-order reflection from the sample and mask is $\Phi(aR_s+bR_m)$.

Flux from the sample and mask then strikes the cavity surface and is reflected back to the sample and mask. Factor c represents the fraction of flux that is reflected from the cavity and not lost due to geometry, edge loss, and other factors. The first-order reflection off the cavity wall is $\Phi(aR_s+bR_m)(cR_c)$.

This flux then strikes the sample and mask for a second time. The second-order reflection from the sample and mask is $\Phi(aR_s+bR_m)^2(cR_c)$. The second-order reflection off the cavity wall is $\Phi(aR_s+bR_m)^2(cR_c)^2$. For purposes of simplification, it is assumed that factors a, b, and c remain the same for all reflections.

Similarly, the third-order reflection from the sample and mask is $\Phi(aR_s+bR_m)^3(cR_c)^2$. While there is an infinite number of reflections within the cavity, within nanoseconds, they reach a steady state that is represented by the above equations. The total light reflected from the sample and mask is:

$$I_{Total}=\Phi(aR_s+bR_m)\Sigma_{n=0}^{n=\infty}[(aR_s+bR_m)(cR_c)]^n \qquad (1)$$

This sum converges if $(aR_s+bR_m)(cR_c)<1$. Assume that $R_s=R_m=R_c=1$, their maximum limit. Then the series converges if $(a+b)c<1$. Since a and b are the fractions of total light received by the fiber-optic receiver, their sum must be less than one, since not all light within the cavity is seen by the numerical aperture (0.5) of the receiving fibers. Since c has similarly been defined as a fraction of one, it can be shown that the series converges to a simple form.

$$I_{Total}=\Phi(aR_s+bR_m)/(1-(aR_s+bR_m)(cR_c)) \qquad (2)$$

Let $\beta$ be the fraction of $I_{Total}$ that is received by the fiber-optic receiver. Then the intensity signal I measured by the instrument will be:

$$I=\beta\Phi(aR_s+bR_m)/(1-(aR_s+bR_m)(cR_c)) \qquad (3)$$

Equation 3 is structurally similar to the formula for the sphere multiplier M in integrating sphere theory, where $p_0$ is the initial reflectance for the incident flux and $p_a$ is the average reflectance for the integrating sphere (see Labsphere Inc., A Guide to Integrating Sphere Theory and Applications, http://www.labsphere.com/uploads/technical-guides/a-guide-to-integrating-sphere-theory-and-applications.pdf).

$$M=p_0/(1-p_a) \qquad (4)$$

Solving Equation 3 for $R_s$ yields the following expression for sample reflectance:

$$R_s=(I-k_1)/(k_2+k_3I) \qquad (5)$$

Where:

$$k_1=\beta bR_m\Phi/(1-bcR_mR_c) \qquad (6)$$

$$k_2=\beta a\Phi/(1-bcR_mR_c) \qquad (7)$$

$$k_3=acR_c/(1-bcR_mR_c) \qquad (8)$$

Equation 5 is referred to herein as the Cavity Model. In this equation, $k_1$ and $k_2$ are linear functions of incident flux $\Phi$, while $k_3$ is independent of $\Phi$. Parameters $k_1$, $k_2$, and $k_3$ are each dependent on the reflectance of the cavity and mask, and are therefore functions of wavelength. For a spectrophotometer based upon the hemispherical 45°/0° measurement geometry described above, using the Cavity Model to calculate the sample's spectral reflectance should correct or substantially correct for sample absorption error. It is important to understand that to use the Cavity Model, an instrument simply must be calibrated on diffuse reflectance standards with known spectra in order to calculate $k_1$, $k_2$, and $k_3$. No quantitative knowledge of $\beta$, a, b, c, $R_m$, or $R_c$ is required.

The most basic conceptual question to ask is whether the measured intensity varies linearly with the illumination intensity. From Equation 3, I is a linear function of incident flux $\Phi$.

Next, consider the measurement of a black sample. For a perfectly black sample, $R_s=0$. Then from Equation 3:

$$I_{Black}=\beta bR_m\Phi/(1-bcR_mR_c) \qquad (9)$$

Comparing Equations 6 and 9 shows that $k_1$ is equal to the measured intensity when the sample is perfectly black. If the reflectance of the mask $R_m=0$, then the measurement of perfect black would be equal to zero.

Next, Equation 5 must be examined to determine if there are conditions for which $R_s$ becomes unbounded. This would occur if $k_2+k_3I=0$. Since I is greater than 0, this could be true only if either $k_2$ or $k_3$ is negative, or if both $k_2$ and $k_3$ are zero. By definition, a, b, and c are less than 1, and $R_m$ and $R_c$ are less than or equal to 1. All are greater than or equal to zero. Therefore, it is true that:

$$1>(1-bcR_mR_c)>0 \qquad (10)$$

From Equations 6, 7, and 8, it follows that:

$$k_1>\beta bR_m\Phi>0 \qquad (11)$$

$$k_2>\beta a\Phi>0 \qquad (12)$$

$$k_3>acR_c>0 \qquad (13)$$

Therefore, neither $k_2$ nor $k_3$ may be negative, and as long as there is incident flux $\Phi$ being reflected from the sample, then $\Phi > 0$ and there are no conditions under which the Cavity Model becomes unbounded.

Finally, the condition in which both the cavity and mask are perfectly non-reflective must be considered. If $R_m = 0$ and $R_c = 0$, then $k_1 = 0$, $k_2 = \beta a \Phi$, and $k_3 = 0$. Equation 3 becomes $I = \beta a \Phi R_s$. This is conceptually valid.

During measurement of the White reflectance standard, there was a noticeable glow of light just outside the area of contact with the test instrument, resulting from the lateral diffusion of light within the translucent Spectralon. This glow was not present during measurement of the opaque Gray and Black standards. When lateral diffusion occurs, there is a corresponding reduction in the intensity of light measured near the edge of the sample, relative to the center of the sample. This decrease in intensity is known as lateral diffusion error (see David L. Spooner, "New method for determining lateral diffusion error in color measurements," Proc. SPIE 2658, Color Imaging: Device-Independent Color, Color Hard Copy, and Graphic Arts, 151 (Mar. 29, 1996)) or edge loss (see J. T. Atkins, F. W. Billmeyer, Jr., "Edge-loss errors in reflectance and transmittance measurements of translucent materials," Materials Research and Standards, 6 (11), (1966)). When measuring a translucent material with different size apertures, using an instrument that fully illuminates and measures through the same aperture, smaller apertures result in lower measured intensities (see Yong-Keun Lee, Bum-Soon Lim, Cheol-We Kim, "Influence of illuminating and viewing aperture size on the color of dental resin composites," Dental Materials, 20 (2), (February 2004)). Very simply, the larger the area being measured, the smaller is the effect of edge loss.

Since the reflectance standards were measured by Labsphere using a 25.4 mm aperture, and the prototype test instrument had a 9 mm aperture, the reflectance spectra $R_{White}$ supplied by Labsphere required downward adjustment to account for increased edge loss during measurement with the prototype instrument.

Let $R'_{White}$ be the adjusted spectral reflectance for the White Standard.

$$R'_{White} = DR_{White}$$

where D (for Diffusion) is the edge loss factor. D is calculated, along with $k_1$, $k_2$, and $k_3$, from measurements of the four reflectance standards with the prototype instrument.

The four reflectance standards were measured to determine $I_{White}$, $I_{50}$, $I_{25}$, and $I_{Black}$. These measured values were combined in Equation 5 with the corresponding Labsphere-supplied spectra for the adjusted White, 50% and 20% Gray, and Black standards ($DR_{White}$, $R_{50}$, $R_{25}$, and $R_{Black}$). The resulting system of four equations was solved at each of the 30 sensor wavelengths to determine $k_1$, $k_2$, and $k_3$ as a function of wavelength, with D initially set to a value of 1. The value of $k_1$ (shown in Equation 9 to equal the measurement of perfect black) was also measured by aiming the spectrophotometer toward a distant diffuse black surface. The spectrum measured for perfect black is from internal light reflecting from the aperture mask ($R_m$). Assuming that the incident flux does not change, $k_1$ must be subtracted from each sample measurement in order to measure the sample spectrum correctly.

Figure 5D:
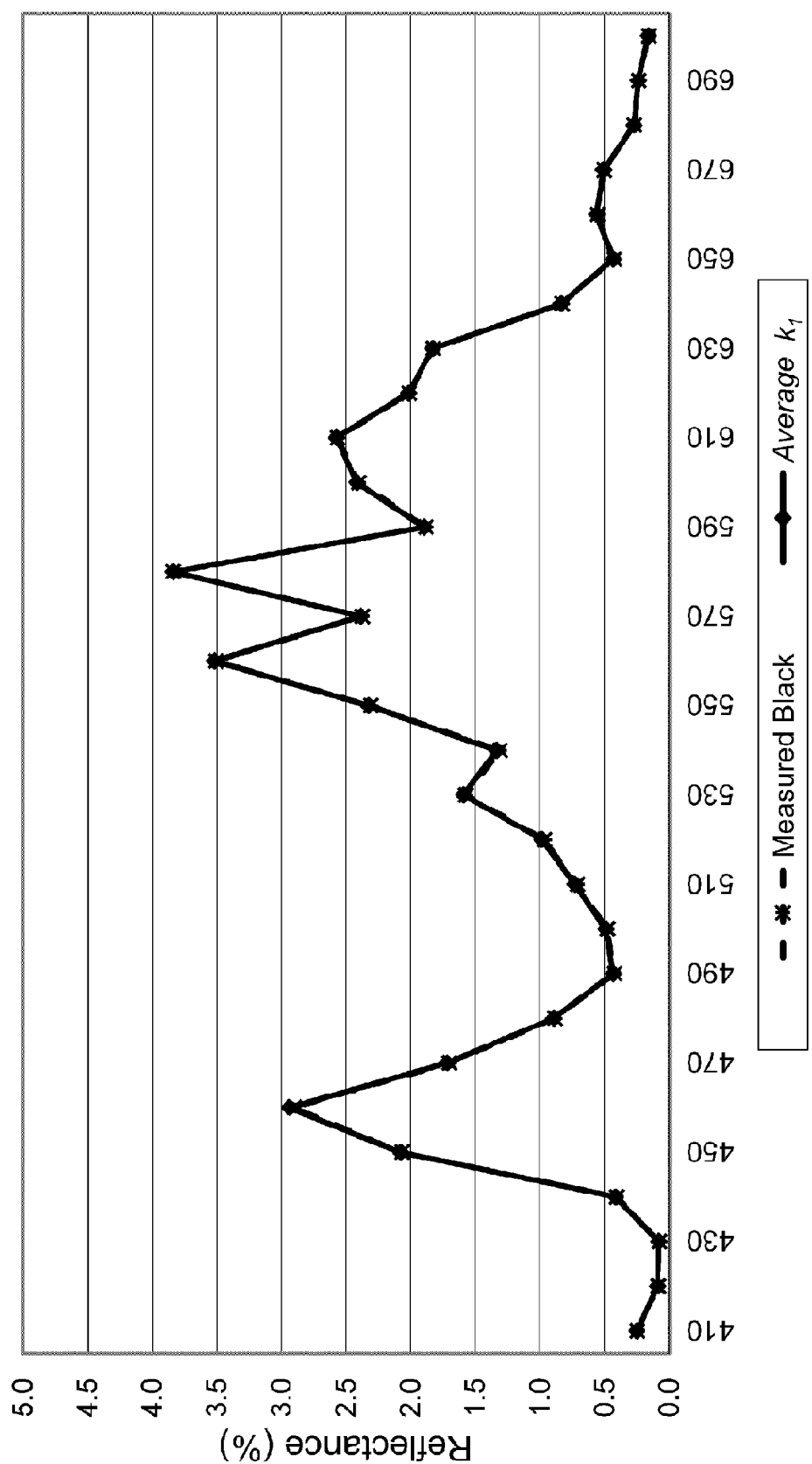
Figure 5E:
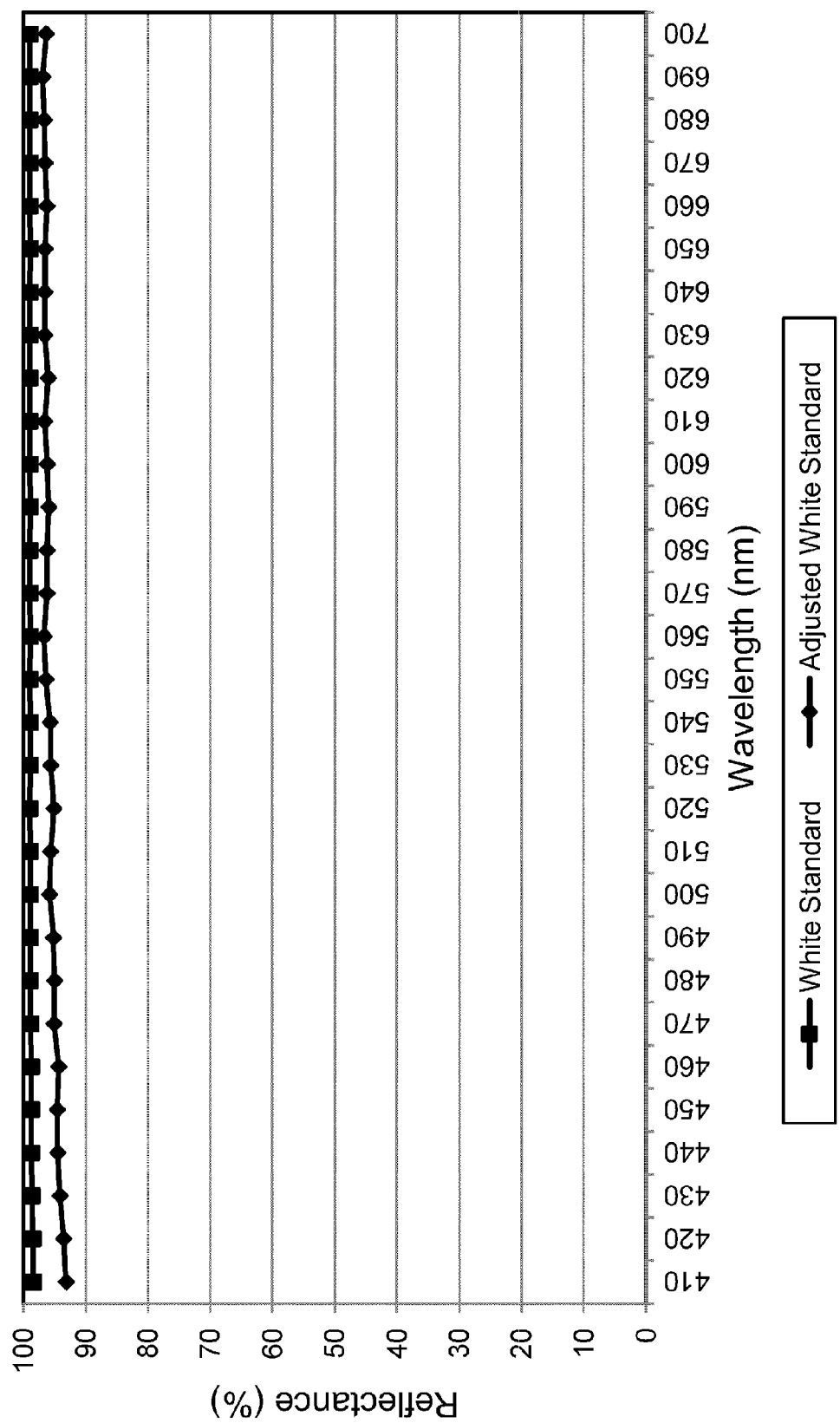

With D=1, solving the system of four equations generates separate values of $k_1$ for each of the four reflectance standards. The edge loss factor D is then determined by goal-seeking to minimize the difference between the four values of $k_1$ at each of the 30 sensor wavelengths. Consistent with the assumptions of the Cavity Model, this goal-seeking converges all four values of $k_1$ to the measured value of simulated perfect black. After calculating D, FIG. 5D shows excellent agreement between measured perfect black and the average of the four calculated $k_1$ values. The color difference between the two, based on CIELAB $\Delta E$ 1994 (D50 illuminant, 2° observer) is 0.1. FIG. 5E shows the Labsphere-supplied spectrum for the White Standard and the adjusted White Standard, using the calculated values of D. The average edge loss is 3.2%, ranging from around 5% in the blue region, to 2% in the red region.

Figure 5F:
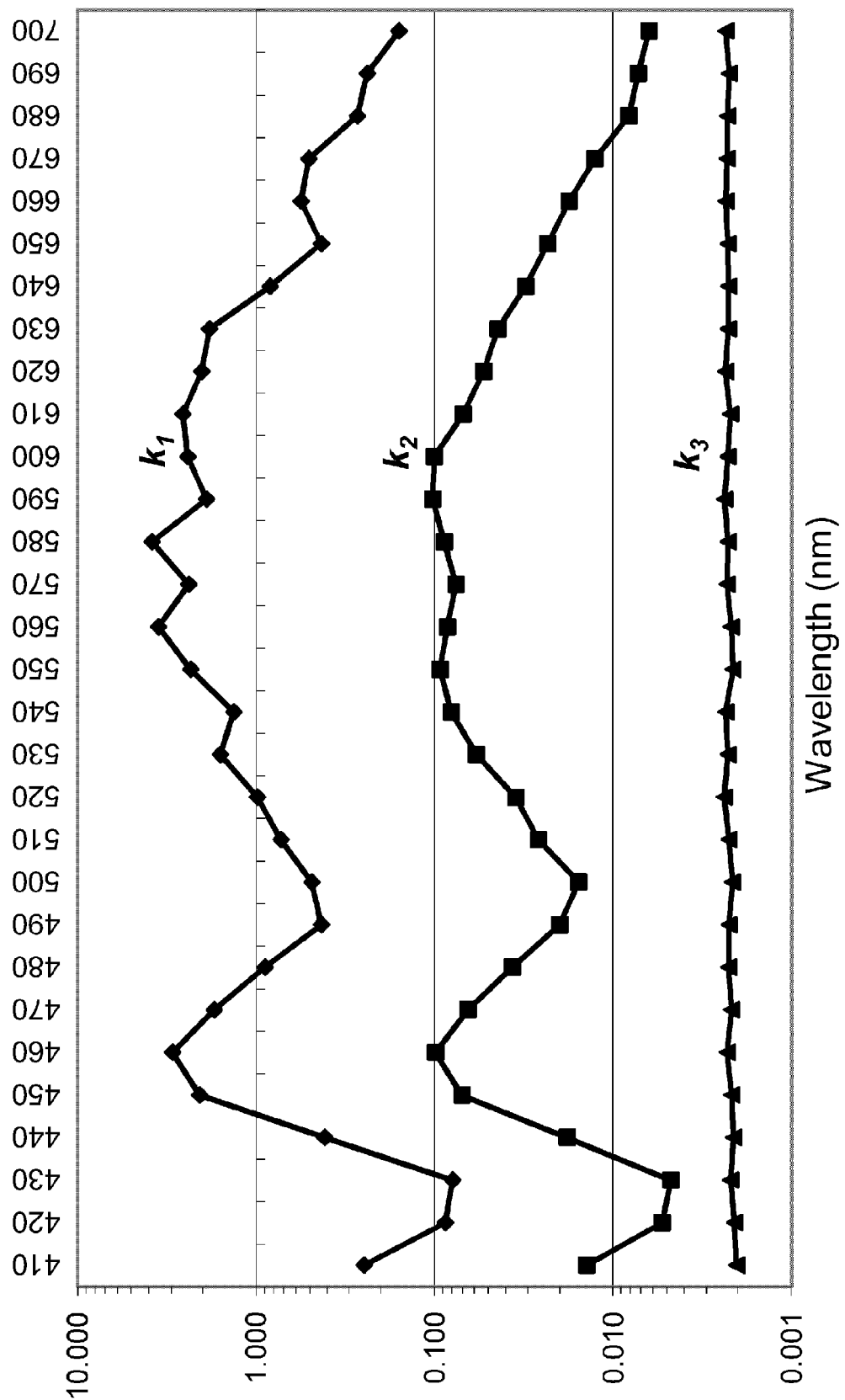

FIG. 5F is a logarithmic plot of the calculated values for $k_1$, $k_2$, and $k_3$. In Equations 6, 7, and 8, $k_1$ and $k_2$ are linear functions of incident flux $\Phi$, while $k_3$ is not a function of $\Phi$. FIG. 5 shows that $k_3$ is relatively flat, while both $k_1$ and $k_2$ show peaks below 410 nm, at 460 nm, and at 570 nm, similar to the general shape of the spectrum of the LED light source in the prototype spectrophotometer. While this suggests agreement with the Model, it does not prove that $k_1$, $k_2$ are linear functions of $\Phi$ or that $k_3$ is independent of $\Phi$.

Table 2 (FIG. 5G) shows the CIELAB $\Delta E$ 1994 color differences between the vendor-supplied spectra for twelve Labsphere Spectralon diffuse reference standards, and measurements of these standards based on (1) linear calibration on White, and (2) calibration and measurement using the Cavity Model. In both cases, the spectrum has been adjusted downward to account for edge loss. The color difference for the White reflectance standard is zero for linear calibration, which is expected since the White standard is the basis for calibration. The large color differences for the gray and color reference standards are the result of sample absorption error.

For the Cavity Model, the color differences are at or near zero for the White, 50% and 20% Gray, and Black standards. This is expected, since all four were used to calibrate the instrument and determine the parameters $k_1$, $k_2$, and $k_3$, and the edge loss for the White reflectance standard.

For the Cavity Model, the average color difference for the eight color reference standards is 1.2. For linear calibration on White, the corresponding average color difference is 3.8. While the just noticeable difference ("JND") varies by color, the mean CIELAB color difference for discrimination has been estimated to be 2.4 (see M. Mahy, L. Van Eycken, A. Oosterlinck, "Evaluation of uniform color spaces developed after the adoption of CIELAB and CIELUV," Color Research and Application, 19 (2)), which is below all measured color differences for linear calibration and greater than all color differences for the Cavity Model.

As will be understood by those of skill in the art, the Cavity Model is a three-parameter equation that provides a methodology for calibrating a single-beam spectrophotometer and correcting for sample absorption error, which is advantageously utilized in accordance with certain preferred embodiments of the present invention. Its use in general requires calibration using a minimum of three reference standards to calculate the three unknown parameters $k_1$, $k_2$, and $k_3$. Measuring four reference standards allows quantification of edge loss in the White Standard, which for a diffuse PTFE reflectance standard can be a significant source of error if it is measured with a smaller aperture than was used for the certified spectrum. A measurement of perfect black (a simulation of infinite empty space) is recommended to verify the calculated value of $k_1$.

FIG. 5A illustrates a Labsphere-supplied spectra for diffuse reflectance standards (with White adjusted for edge loss) and corresponding measured values for those standards using linear calibration on the White standard. FIG. 5C illustrates a hemispherical 45°/0° measurement cavity with interior surface reflectance spectra for sample, cavity, and mask of Rs, Rc, and Rm, respectively. FIG. 5D illustrates measured perfect black (simulated empty space) and the average k1 calculated from measurements of the White (adjusted for edge loss), 50% Gray, 20% Gray, and Black reflectance standards. FIG. 5E illustrates spectra for the White Reflectance Standard, supplied by Labsphere and adjusted for edge loss. FIG. 5F illustrates parameters k1, k2, and k3 for the Cavity Model, calculated from measurements of White (adjusted for edge loss), 50% Gray, 20% Gray, and Black reflectance standards.

The paper entitled "Correction of single-beam sample absorption error in a hemispherical 45°/0° spectrophotometer measurement cavity" by Walter W. Sloan is hereby incorporated by reference.

In machine learning and statistics, "classification" is a methodology for assigning objects to predefined categories. An algorithm that implements classification is known as a "Classifier" and is developed from a set of training data by identifying a set of categories for sub-populations ("Classes") of the data. Each class is defined by one or more quantifiable properties that are referred to as "Explanatory Variables" or "Features." A Classifier is a learning system in that additional data input can be used to adjust the Explanatory Variables and develop new heuristics that improve the accuracy of data classification.

Figure 6A:
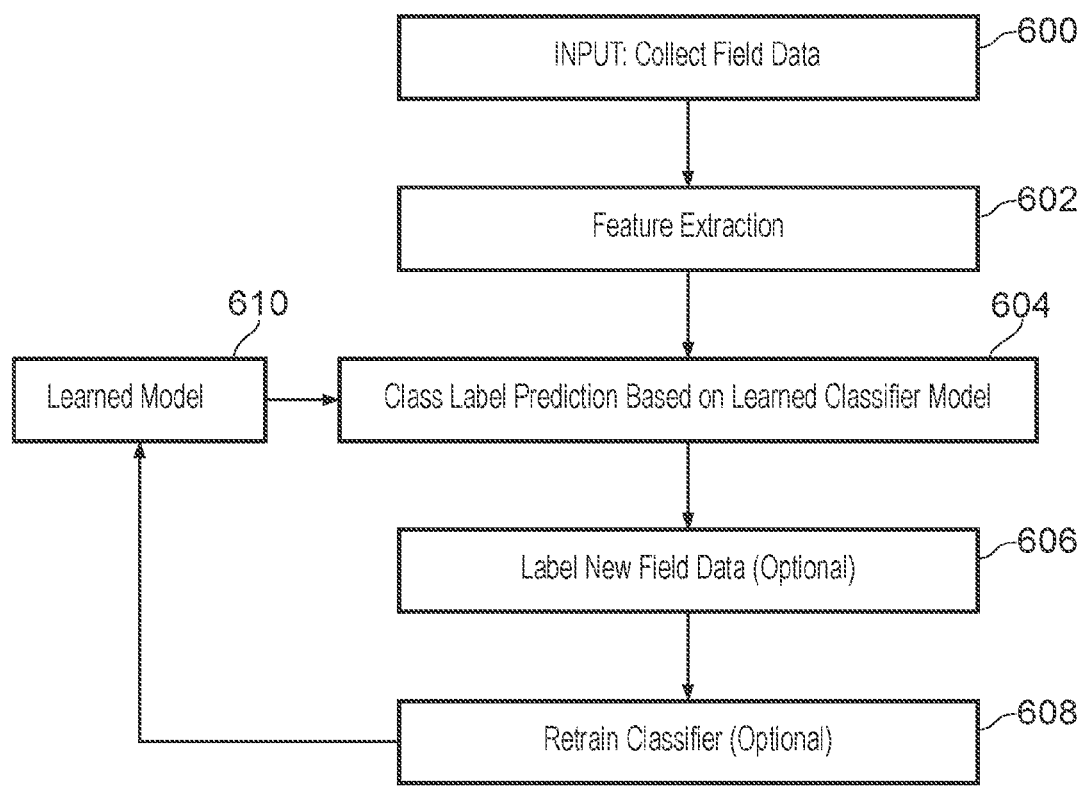
FIGS. 6A, 6B, 6C, 6D, 6E, 6F, 6G and 6H illustrate principles and aspects of classifier based methods in accordance with certain preferred embodiments of the present invention.

FIG. 6A is a generalized flow chart for developing and updating a Classifier. Data is collected (600) and Features (Explanatory Variables) are extracted from the data (602) and used for class label prediction (604). Additional data may be collected and classified (606), and used to retrain the Classifier (608) by adjusting the Explanatory Variables or adding additional heuristics. The Learned Classifier Model (610) is then used for class label prediction.

Figure 6B:
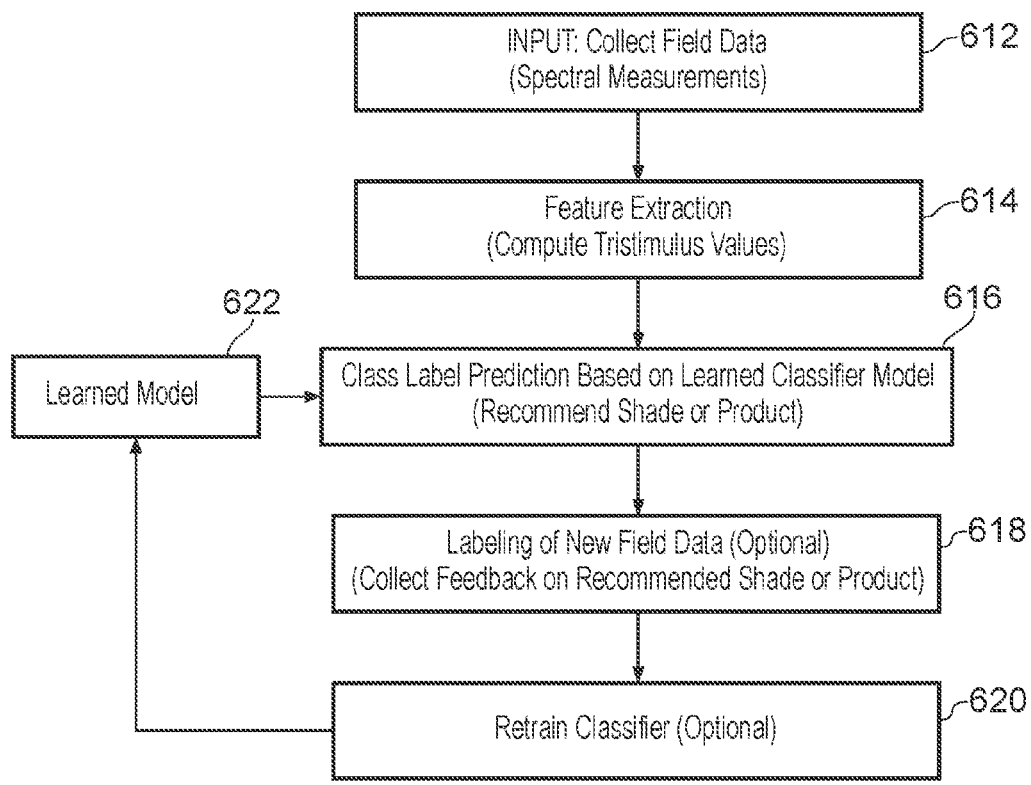

FIG. 6B is a flow chart for developing and updating a Classifier for shade recommendation. Field data is collected in the form of spectral measurements (612) and Features are extracted (614) in the form of the tristimulus calculations for Lightness, Chroma and hue ($L^*$, $C^*$ and $h^*$). The Features are used for class label prediction (616). Additional data may be collected and classified (618), and used to retrain the Classifier (620) by adjusting the Explanatory Variables or adding additional heuristics. The Learned Model (622) is then used for class label prediction.

In an alternate preferred embodiment, features are extracted from the field data spectra in the form of other tristimulus calculations (for example CIELAB). These features are then used for class label prediction. In still another alternate preferred embodiment, particular wavelength-dependent spectral reflectance measurements of interest are used directly for the class label prediction. In this embodiment, measurements of interest are optionally determined manually or through an automated method of pertinent feature extraction such as principal component analysis.

In still another preferred embodiment, particular features are extracted from the field data spectra by transforming the spectra into measurements known to be relevant based on the pigment composition(s) of the target measurement substrate. In the case of skin measurement, particular chromophores are known in the literature of skin spectroscopy to be principally responsible for the color appearance of skin: oxyhaemoglobin, deoxyhaemoglobin, and melanin. Reflectance spectra are converted to absorbance spectra, and relative concentrations of these chromophores are determined using formulae from the literature (see: Stamatas, G. N., Zmudzka, B. Z., Kollias, N., & Beer, J. Z. (2008). In vivo measurement of skin erythema and pigmentation: new means of implementation of diffuse reflectance spectroscopy with a commercial instrument. British Journal of Dermatology, 159(3), 683-690.) These chromophore concentration variables are used as features for the class label prediction. In an alternate preferred embodiment, combinations of previously described features extracted from spectra are used for class label prediction.

Figure 6C:
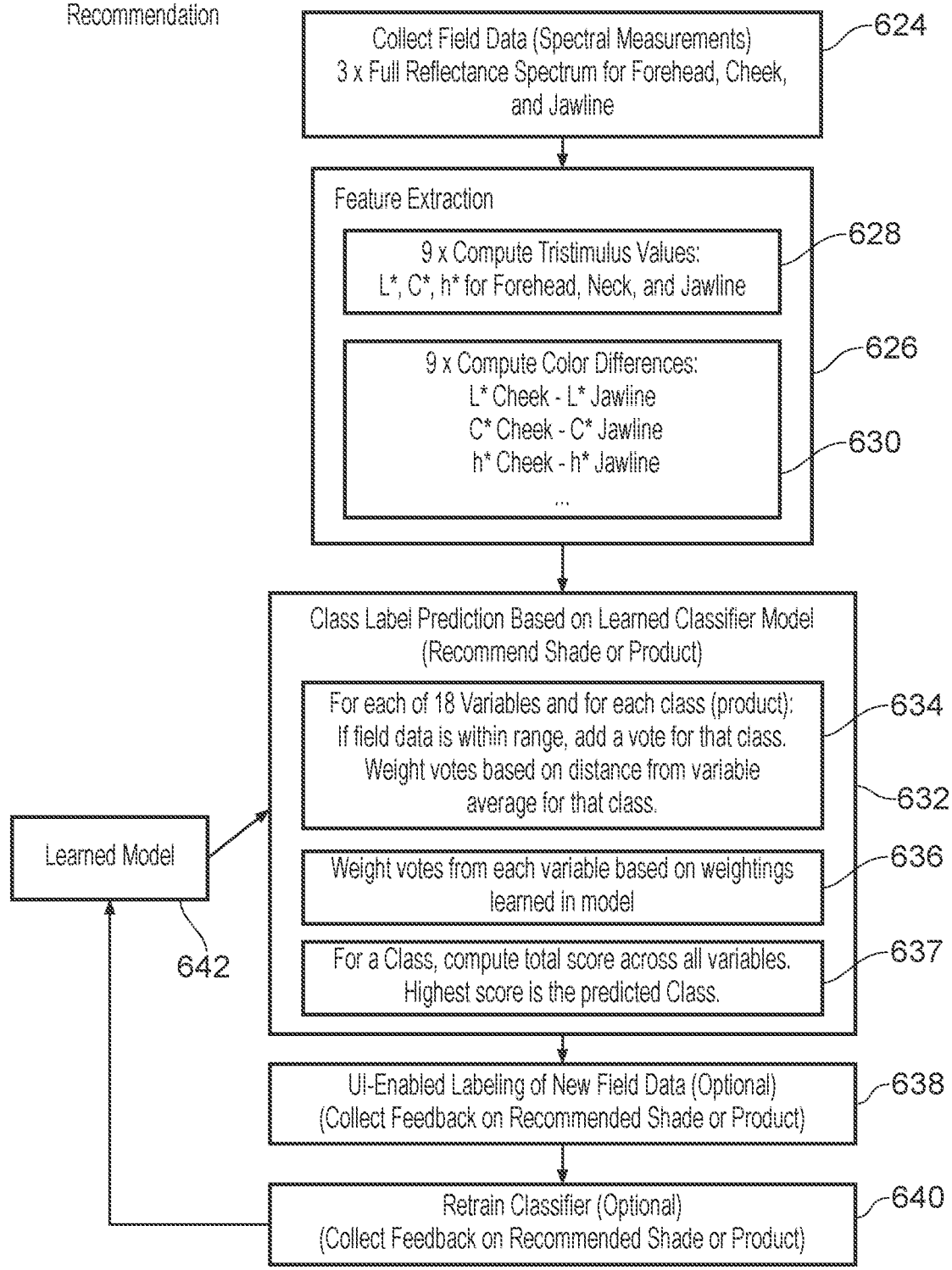
Figure 6D:
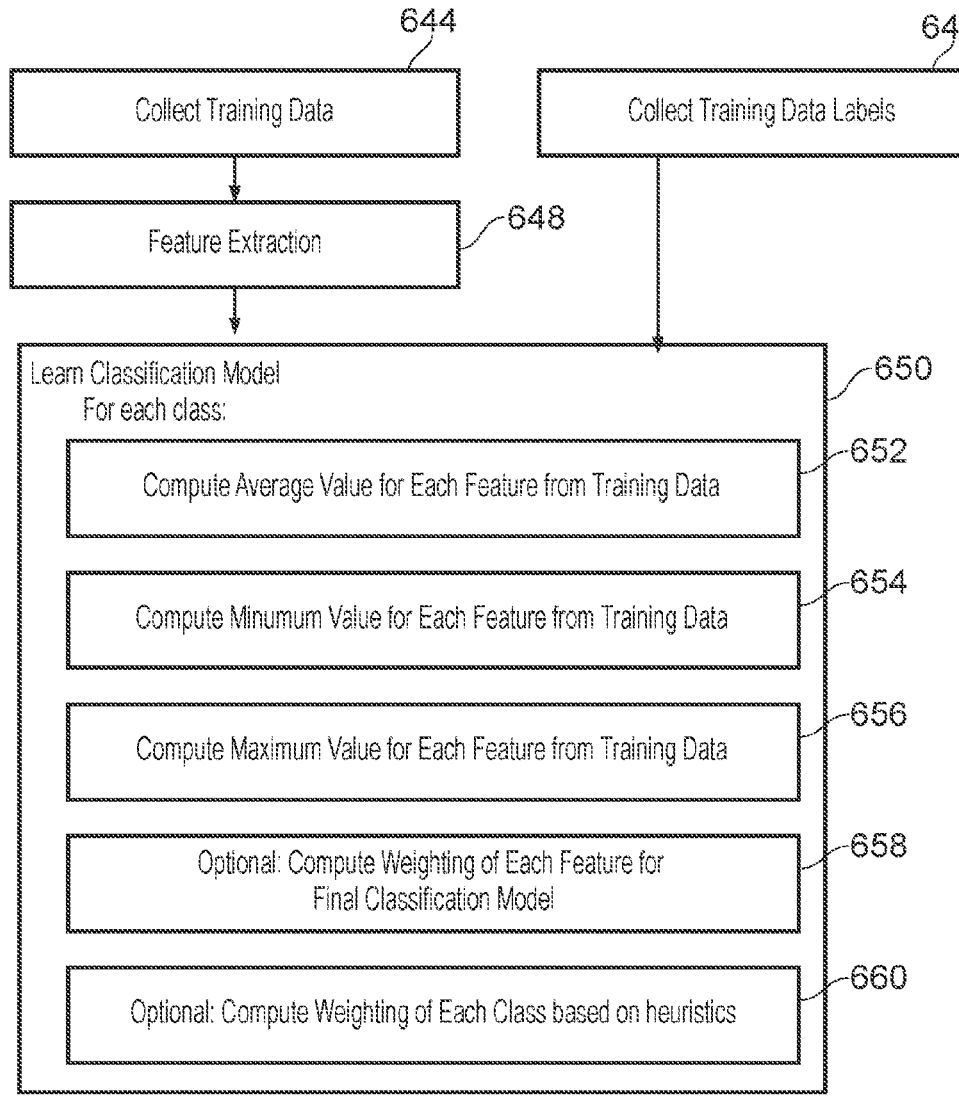

FIG. 6D is a generalized flow chart for a Range-Based Classifier. The Classification Model 650) is developed (Learned) from the Features (648) that are extracted from the training data (644), and the training data labels (646). Features are assigned to classes according to the training data labels. To build (Learn) the Classification Model for each class, the following calculations are performed for each Feature from the training data:

Average value (652).
Minimum value (654)
Maximum value (656)
Compute weighting factor from regression (658) (OPTIONAL)
Compute weighting factor from heuristics (660) (OPTIONAL)

Figure 6E:
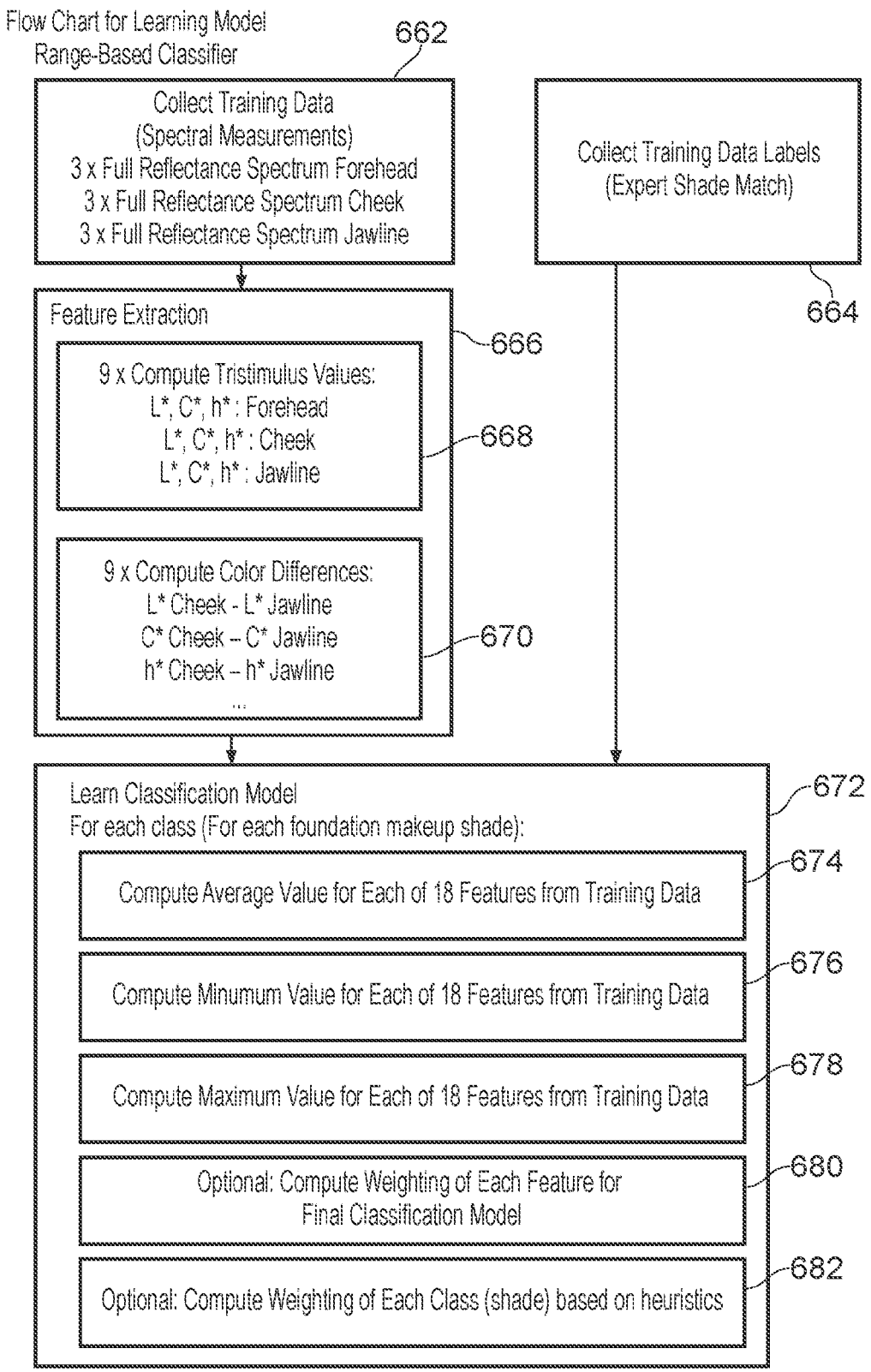

FIG. 6E is a flow chart for the Learning Model for the Range-Based Classifier in this disclosure. Training Data is collected by measuring the full reflectance spectrum of the training subject's forehead, Jawline, and jawline (662). Eighteen Features are extracted from the training data (666).

Compute tristimulus values ($L^*$, $C^*$, $h^*$) for the Forehead, Cheek, and Jawline (668).

For each tristimulus value ($L^*$, $C^*$, $h^*$), compute the color difference (670).

Cheek—Jawline
Cheek—Forehead
Jawline—Forehead

The Classification Model (672) is developed (Learned) for each of the classes (foundation makeup shade) by calculating ranges and averages of each of the Features.

Compute Average Value for each of the 18 Features from the Training Data (674).

Compute Minimum Value for each of the 18 Features from the Training Data (676).

Compute Maximum Value for each of the 18 Features from the Training Data (678).

(Optional) Compute the weighting of each Feature based on regression (680).

(Optional) Compute the weighting of each Feature based on heuristics (682).

FIG. 6C is a flow chart for client shade recommendation, based on the Classifier described in 6E. Field Data is collected by measuring the full reflectance spectrum of a subject's Forehead, Cheek, and Jawline (624). Eighteen Features are then extracted from the Field Data (626).

Compute tristimulus values ($L^*$, $C^*$, $h^*$) for the Forehead, Cheek, and Jawline (628).

For each tristimulus value ($L^*$, $C^*$, $h^*$), compute the color difference (630).

Cheek—Jawline
Cheek—Forehead
Jawline—Forehead

The Learned Classification Model (642) is used to assign subjects to classes (foundation makeup shades) by comparing the subject Features with the ranges and averages of each of the classes (632). Each class has its own Minimum, Maximum, and Average for each of the 18 Features.

For each of the 18 Features, if the Field Data is within range, compute a score for that Feature. The score is dependent on its distance from the average for the class, ranging from one at the average, and decreasing to zero at the minimum or maximum of the range. (634).

The Learned Model (642) has weighting factors for each of the Features. Multiply the weighting factor for a feature by the score for that feature. Compute the total weighted score for all Features. This is the total score for the class. (636)

Compare the total scores for each of the classes. The highest score is the predicted class for the measured subject. (637)

If the subject feedback is positive with respect to the shade-match of the predicted class (foundation makeup shade), label the Field Data with the predicted class. (638) (OPTIONAL)

Retrain the classifier by adding the captured Field Data (640).

Figure 6F:
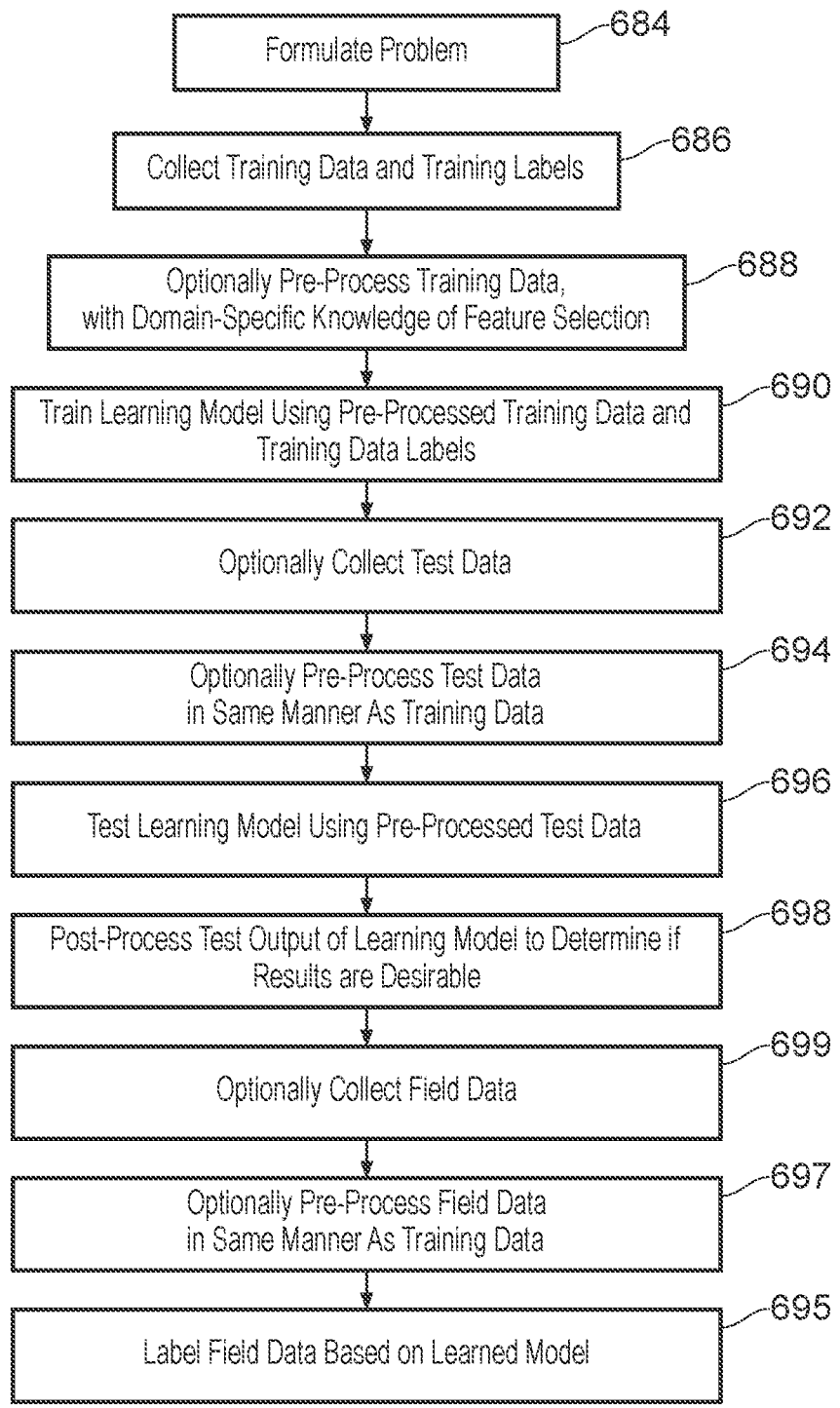

FIG. 6F is a generalized Flow Chart for a linear embodiment of a Classifier Model, showing formulation of the classification problem (684), collection of training data and training labels (686), optionally pre-processing the training data and using that data to train the Learning Model (688, 690), optionally collect and pre-process test data in the same manner as the training data (692, 694), test the Learning Model and determine if the results are desirable (696, 698), and optionally collect and test Field Data in the same manner as the training data (699, 697, and 695). This linear embodiment of a classifier does not call for continual adjustment of the Learning Model as Field Data is acquired and processed.

Figure 6G:
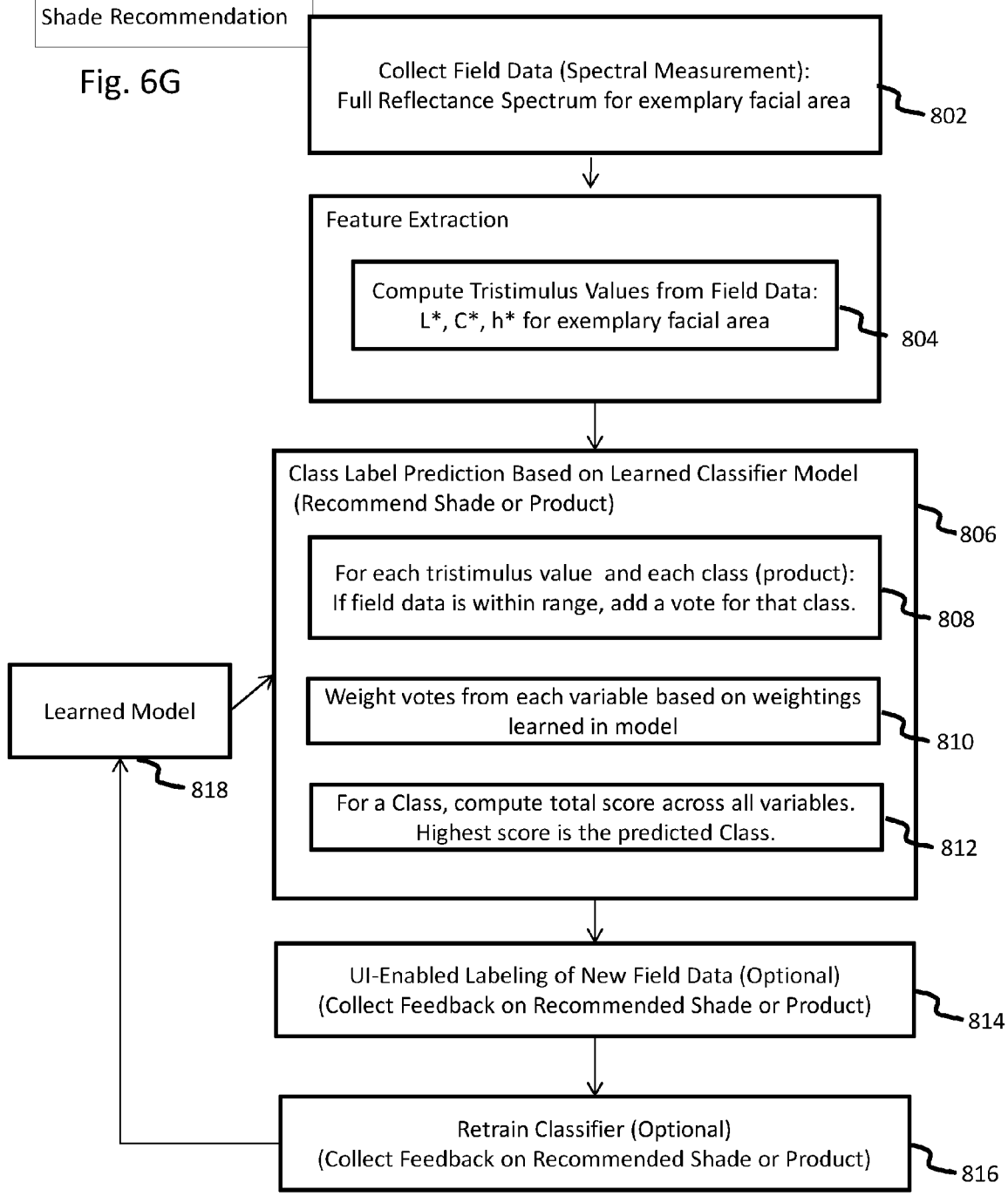
Figure 6H:
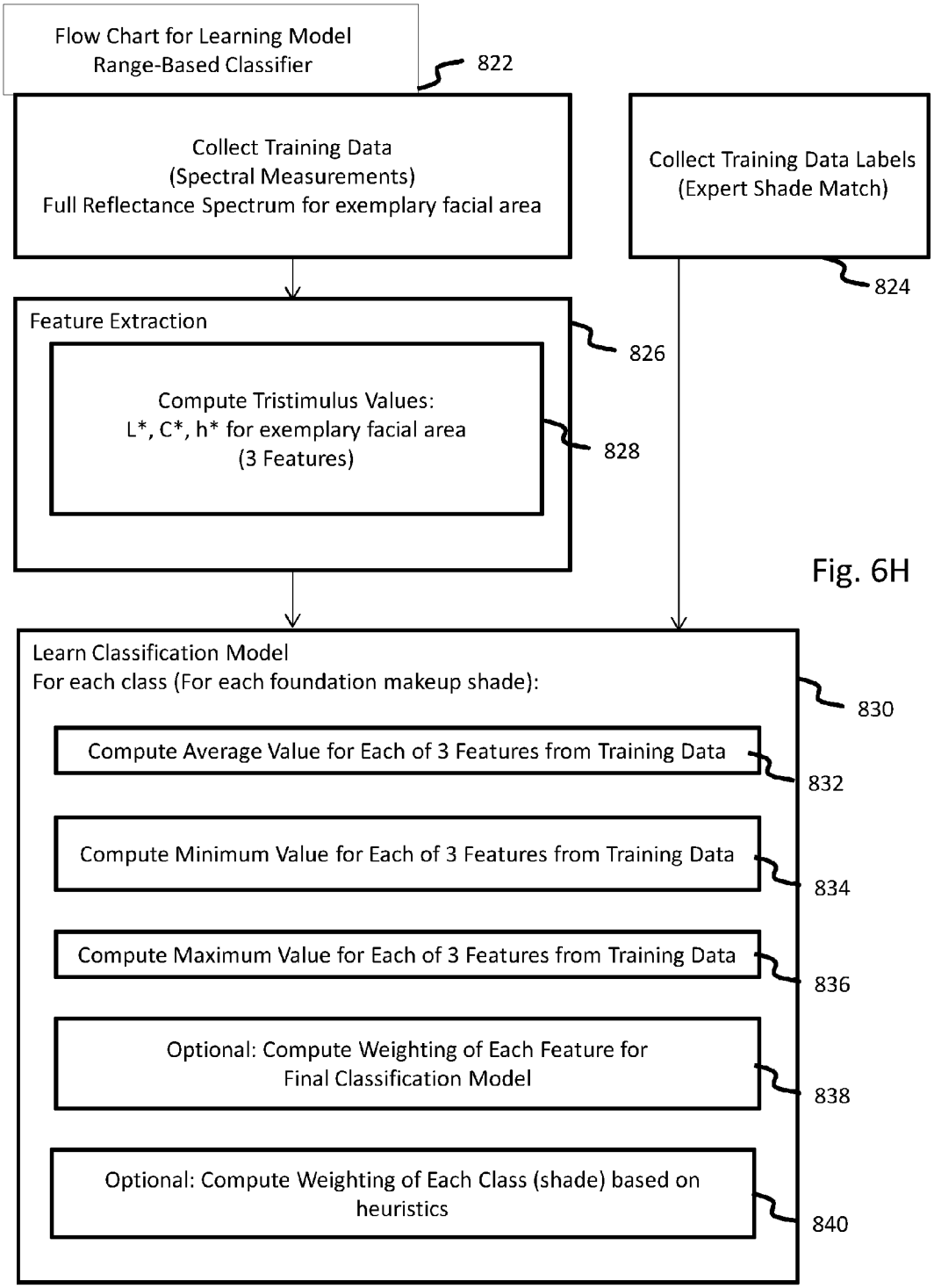

FIG. 6H is a flow chart for an alternative embodiment of a Learning Model for a Range-Based Classifier based on a single exemplary measurement area (e.g., a facial area) in accordance with the present invention. Training Data is collected by measuring a preferably full reflectance spectrum of the training subject's exemplary measurements area (882). Preferably three Features are extracted from the training data (826), although alternatively other numbers of Features could be extracted, as a particular example $L^*$, $C^*$, $h^*$, as well as other tristimulus values such as $L^*$, $a^*$, $b^*$, which also could result in five Features ($L^*$, $C^*$, $h^*$, $a^*$, $b^*$). As illustrated by 828, in certain embodiments only $L^*$, $C^*$, $h^*$ are extracted, although $L^*$, $a^*$, $b^*$ could be substituted therefor)

Compute tristimulus values ($L^*$, $C^*$, $h^*$) for the measurement area (828).

The Classification Model (830) is developed (Learned) for each of the classes (e.g., foundation makeup shade or other targets such as paint or ink formulations) from the Features extracted (826/828) and the collected training data labels which are used to associate the training data with the classes. To build (Learn) the Classifier, the following calculations are performed for each class:

Compute Average Value for each of the three Features from the Training Data (832).

Compute Minimum Value for each of the three Features from the Training Data (834).

Compute Maximum Value for each of the three Features from the Training Data (836).

(Optional) Compute the weighting of each Feature based on regression (838).

(Optional) Compute the weighting of each Feature based on heuristics (840).

FIG. 6G is a flow chart for client shade recommendation, based on the Classifier described in 6H. Field Data is collected by measuring preferably the full reflectance spectrum of a measurement area, which may be an exemplary facial area (802). Preferably three Features (or alternatively five Features, etc.) are then extracted from the Field Data (804), which may be computed tristimulus values ($L^*$, $C^*$, $h^*$) for the measurement area.

The Learned Classification Model (818) is used to assign subjects to classes (e.g., foundation makeup shades) by comparing the subject Features with the ranges and averages of each of the classes (806). Each class has its own Minimum, Maximum, and Average for each of the preferably three Features.

For each of the three Features, if the Field Data is within range, compute a score for that Feature. The score is dependent on its distance from the average for the class, ranging from one at the average, and decreasing to zero at the minimum or maximum of the range. (808).

The Learned Model (818) preferably has weighting factors for each of the Features. Multiply the weighting factor for a feature by the score for that feature. Compute the total weighted score for all Features. This is the total score for the class. (810)

Compute and compare the total scores for each of the classes. The highest score is the predicted class for the measured subject. (812)

If the subject feedback is positive with respect to the shade-match of the predicted class (foundation makeup shade), label the Field Data with the predicted class. (814) (OPTIONAL)

Optionally, the classifier may be retrained by adding the captured Field Data (816).

Non-limiting examples for which the use of a classification model for color shade-matching may be superior to variations of Euclidian distance in color space for shade-matching (e.g. Delta E, Delta E 1994, Delta E CMC) include the measurement of samples in which texture can affect the perception of color (e.g. textiles, wood, masonry, fruits, vegetables), samples for which the target for shade matching is a tool for coloration that is dependent on application technique (e.g. cosmetics, hair coloring), and samples that are subject to metamerism.

As described elsewhere herein, preferred embodiments of the present invention desirably include a display, preferably an LCD, for conveniently providing graphic, textual and numeric information to users to provide an intuitive and powerful user interface. Such a display, in combination with the preferred arrangement of an upper button 9 and preferably three low buttons 9 (see, e.g., FIG. 2A), enable preferred embodiments to provide such an intuitive and powerful user interface.

Figure 7A:

Referring now to FIG. 7A et seq., exemplary screen shots that are displayed in accordance will now be described. Based on the exemplary screen shots illustrated and described herein, it will be understood to those of skill in the art that refinements, variations and alterations thereof are within the scope of the present invention.

As illustrated in FIG. 7A, an introductory screen desirably is displayed. This screen may, for example, provide company or product identifiers, and graphics of a desirable type, etc. Preferably, a start indicator is displayed proximal to one of buttons 9 (e.g., lower center button 9), and the start of operation by pressing of the appropriate button 9.

Figure 7B:
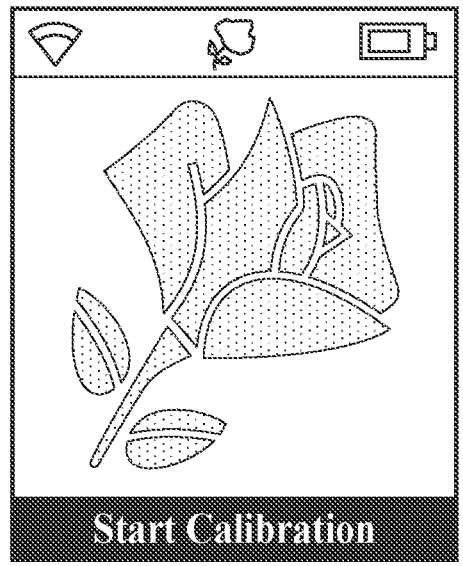

As illustrated in FIG. 7B, in preferred embodiments a calibration start screen is displayed. Preferably, a calibration start indicator is displayed proximal to one of buttons 9 (e.g., lower center button 9), and the start of calibration is initiated by pressing of the appropriate button 9.

Figure 7C:
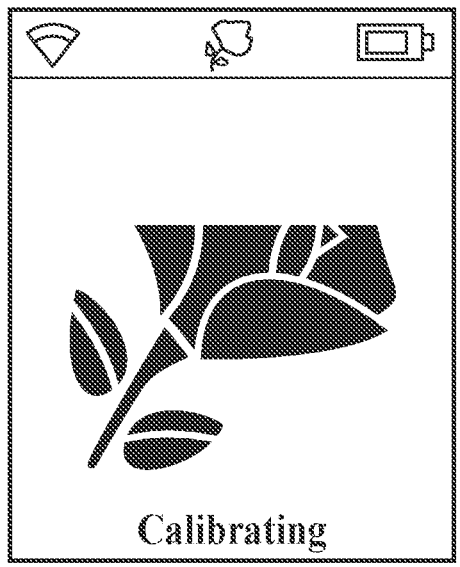

As illustrated in FIG. 7C, in preferred embodiments a calibrating screen is displayed, which desirably indicates to the user that the calibration process is underway.

Figure 7D:
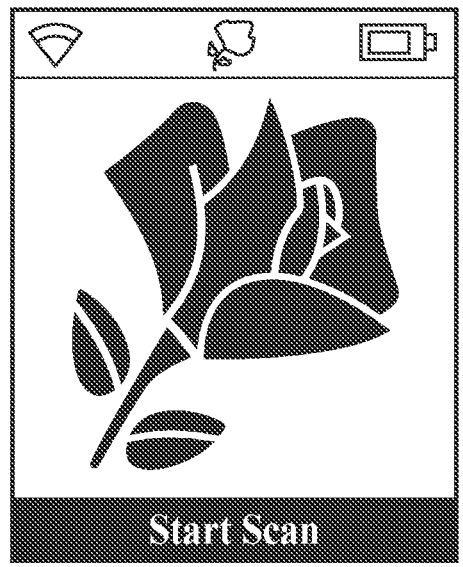

As illustrated in FIG. 7D, in preferred embodiments a start screen is displayed, which indicates that the calibration process has successfully completed in the event of an unsuccessful calibration, desirably a screen is displayed that prompts the user to initiate calibration. In alternate preferred embodiments, the calibration sequence is initiated a plurality of times before the user is prompted to re-initiate calibration, and still alternatively additional messages might be displayed, such as a prompt for power down, technician servicing, cleaning or other maintenance of the calibration reference, etc. Preferably a start scan indicator is displayed proximal to one of buttons 9 (e.g., lower center button 9), and the start of further processing is initiated by pressing of the appropriate button 9.

Figure 7E:
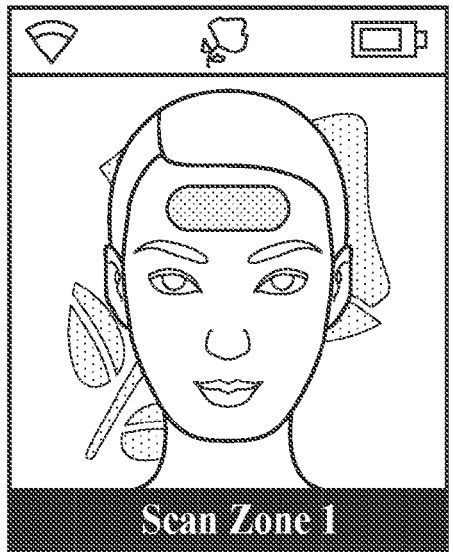

As illustrated in FIG. 7E, in preferred embodiments a scan zone 1 screen is displayed. Preferably an indicator to start a zone 1 scan is displayed proximal to one of buttons 9 (e.g., lower center button 9), and the start of the scan is initiated by pressing of the appropriate button 9. In preferred embodiments, as illustrated a graphic is displayed that guides the user to the approximate location of the zone 1 scan. It should be noted that, in preferred embodiments, a start of scan initiates a plurality of measurements with a single activation, such as three measurements. In certain of such embodiments, an average is taken of the three measurements, spectral band by spectral band. In other embodiments, $L^*$, $a^*$, $b^*$, or $L^*$, $C^*$, $h^*$, values are calculated and averaged. What is important is that in such embodiments a plurality of measurements may be used and averaged to increase data integrity and reliability.

Figure 7F:
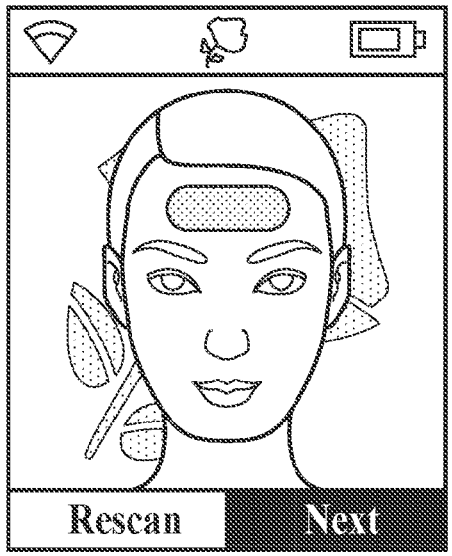

As illustrated in FIG. 7F, in preferred embodiments a screen is displayed that enables the user to rescan zone 1 or proceed to the next step. Preferably the rescan and next indicators are displayed proximal to corresponding one of buttons 9 (e.g., lower left and right buttons 9), and the rescan or progression to the next step is selected by pressing of the appropriate button 9.

Figure 7G:
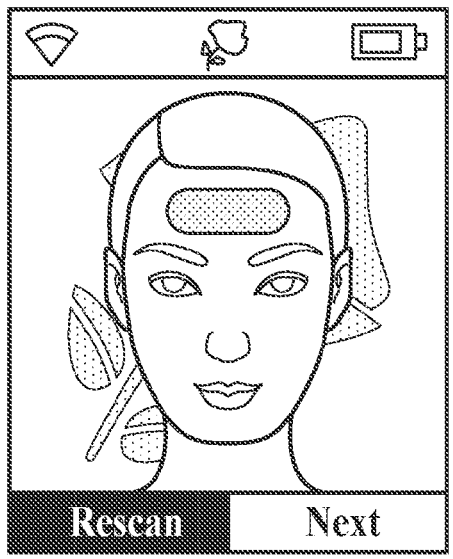

FIG. 7G is similar to FIG. 7F but in FIG. 7F the next indicator is highlighted, while in FIG. 7G the rescan indicator is highlighted. In preferred embodiments, once a selection is highlighted, activation of the selected action is initiated by a predetermined one of buttons 9 (e.g., lower center button 9).

Figure 7H:
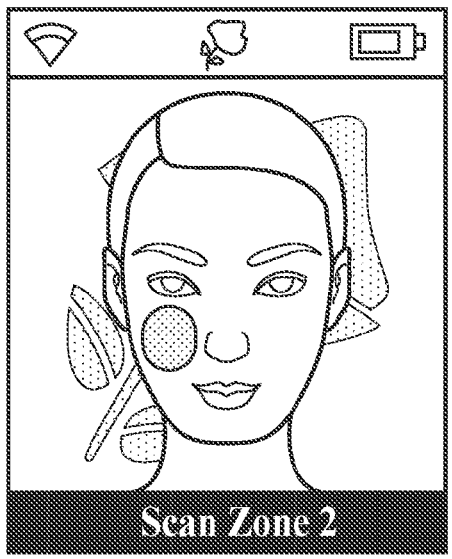

As illustrated in FIG. 7H, in preferred embodiments a scan zone 2 screen is displayed. Preferably an indicator to start a zone 2 scan is displayed proximal to one of buttons 9 (e.g., lower center button 9), and the start of the scan is initiated by pressing of the appropriate button 9. In preferred embodiments, as illustrated a graphic is displayed that guides the user to the approximate location of the zone 2 scan.

Figure 7L:
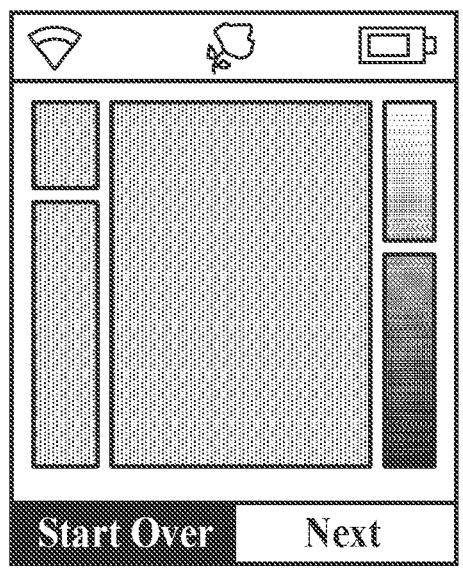
Figure 7M:
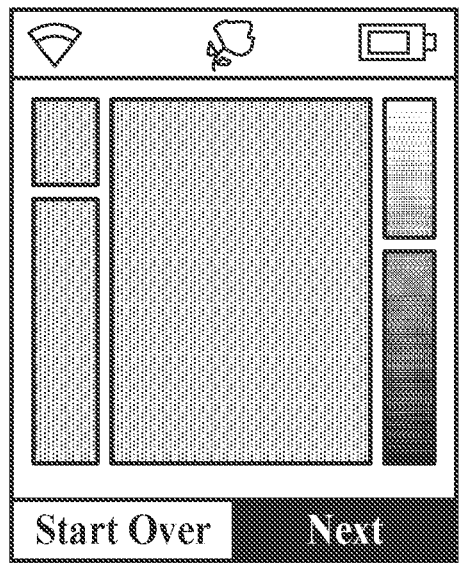
Figure 7N:
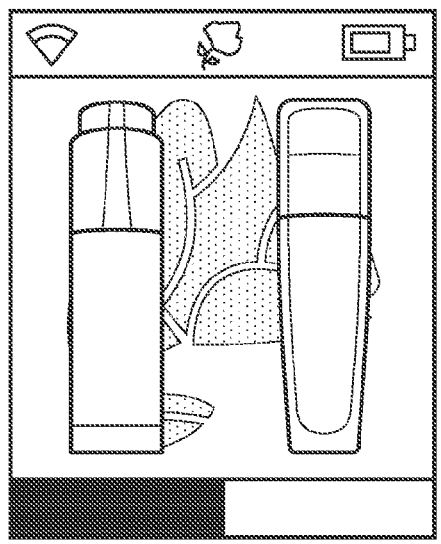
Figure 7O:
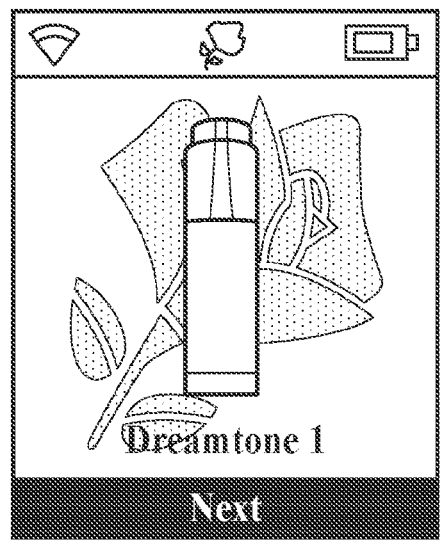
Figure 7P:
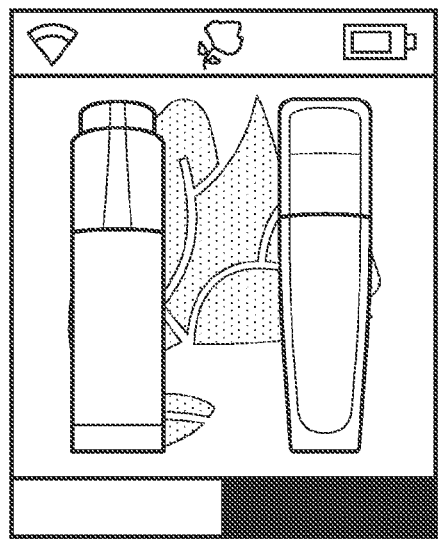
Figure 7Q:
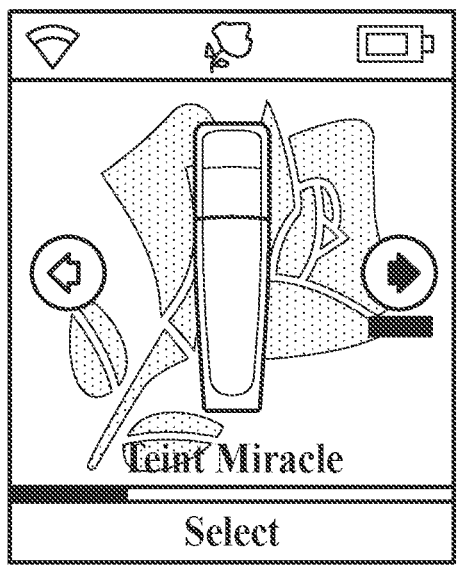
Figure 7R:
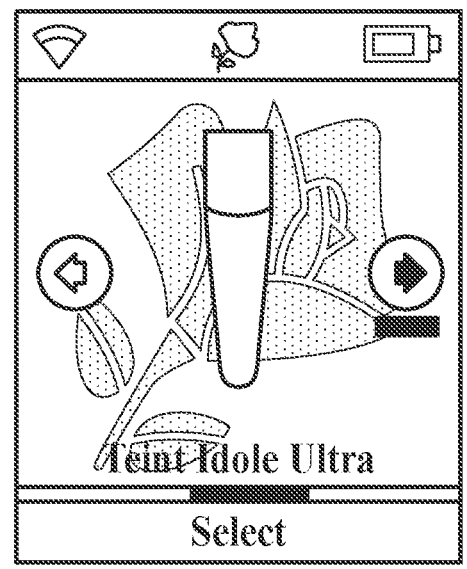
Figure 7S:
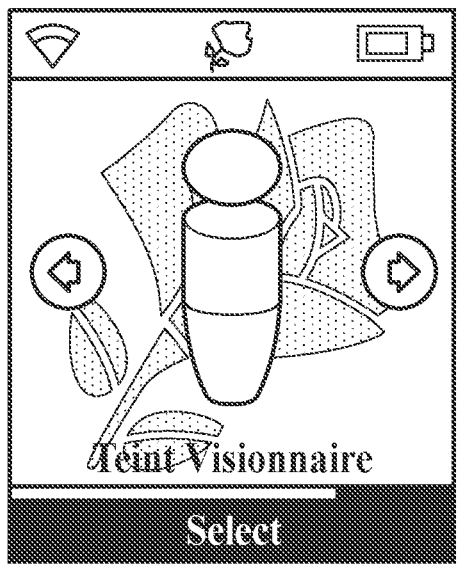
Figure 7T:
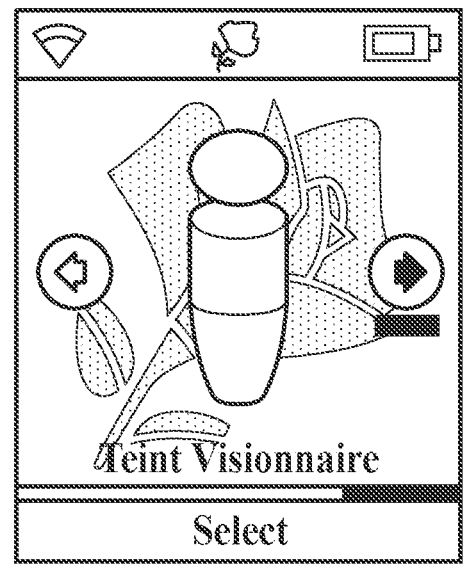
Figure 7U:
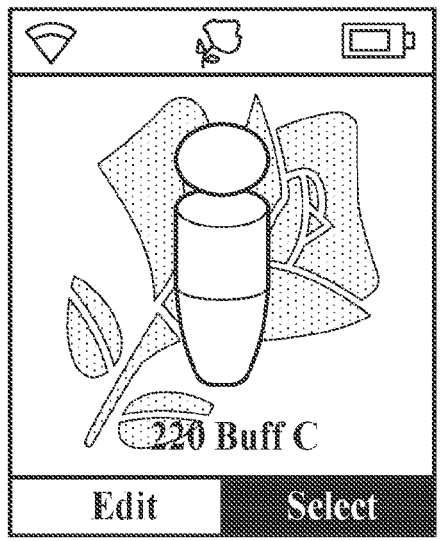
Figure 7V:
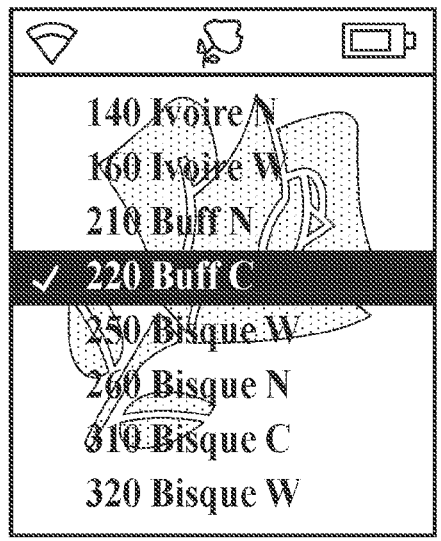
Figure 7W:
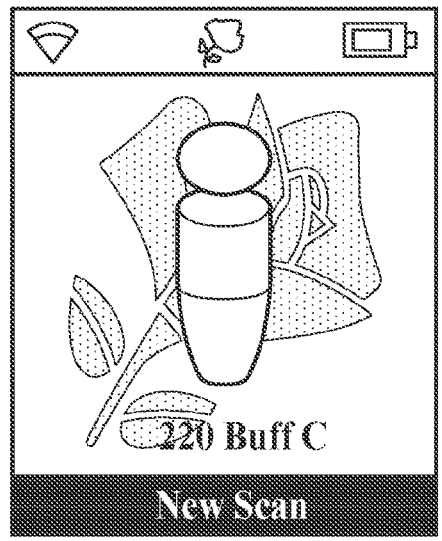
Figure 7X:
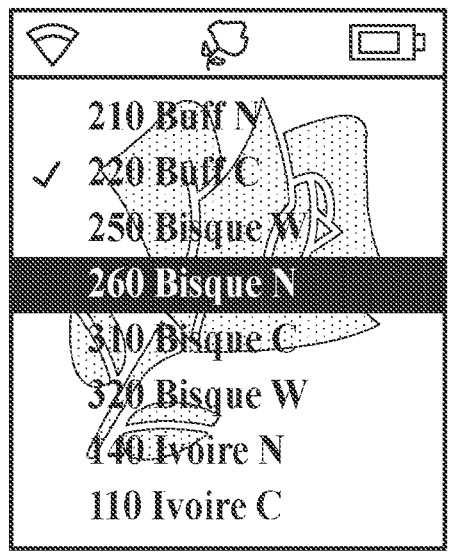
Figure 7Y:
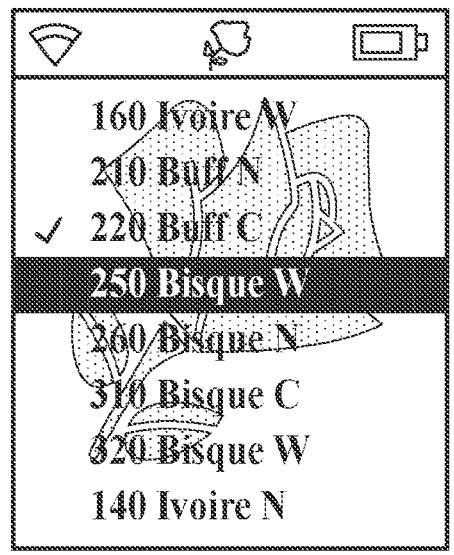
Figure 7Z:
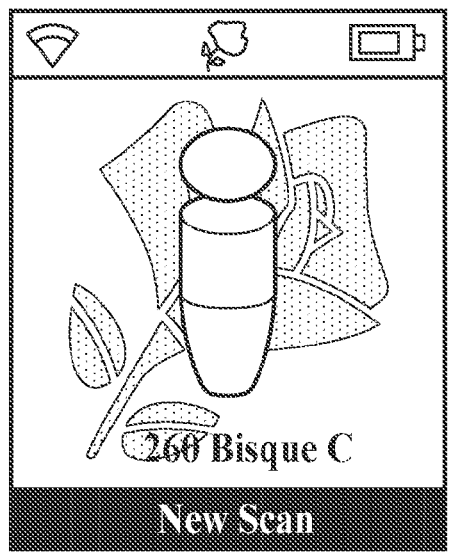
Figure 7A:
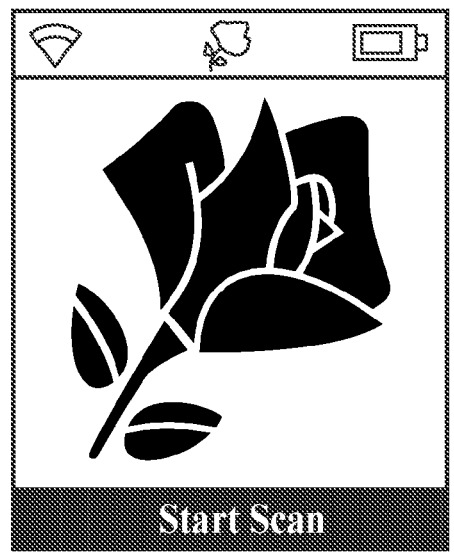
Figure 7B:
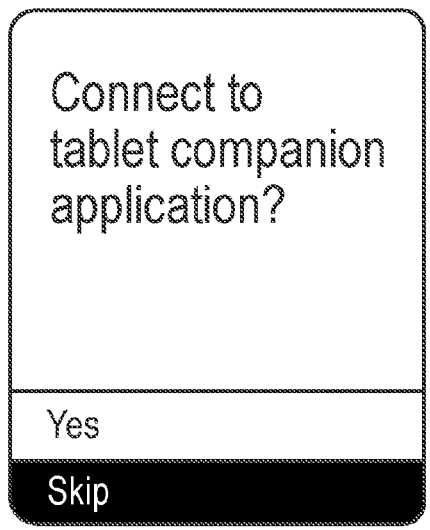
Figure 7C:
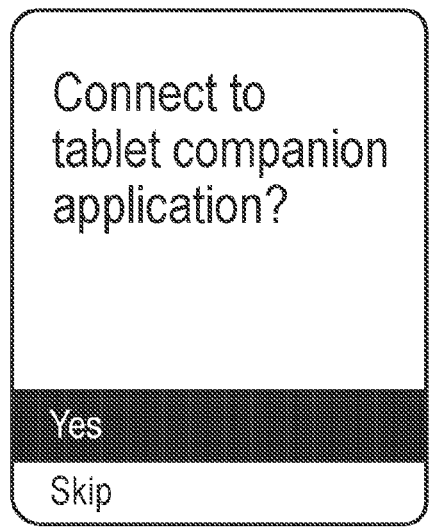
Figure 7D:
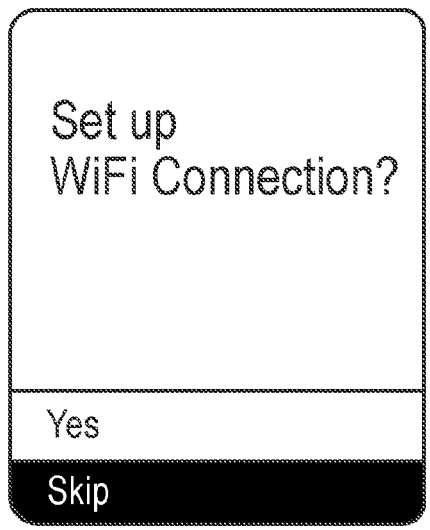
Figure 7E:
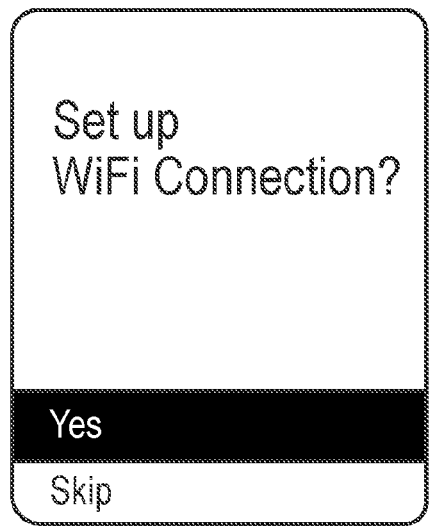
Figure 7F:
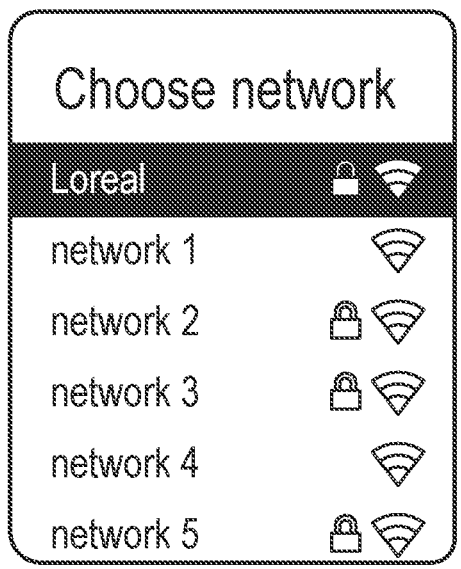
Figure 7G:
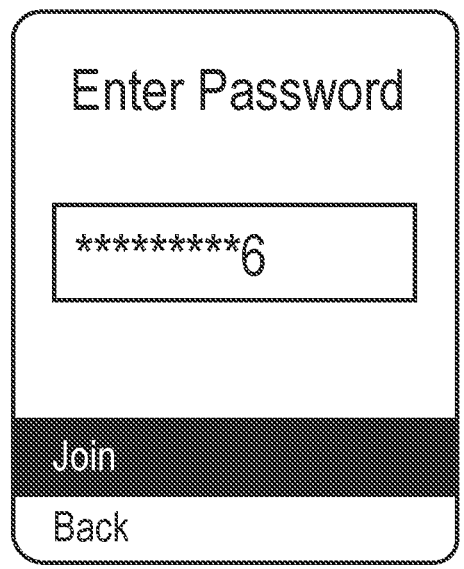
Figure 7H:
Figure 7I:
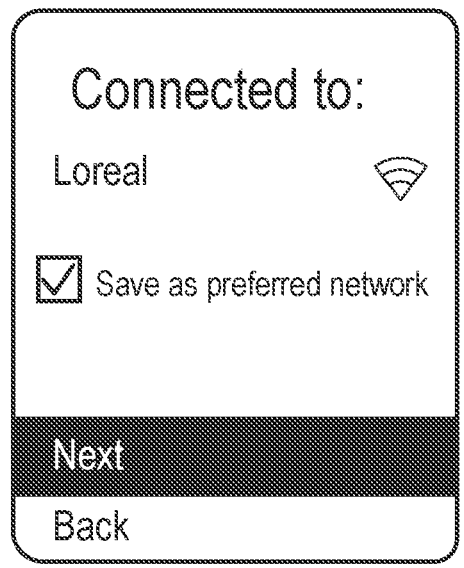
Figure 7N:
Figure 7O:
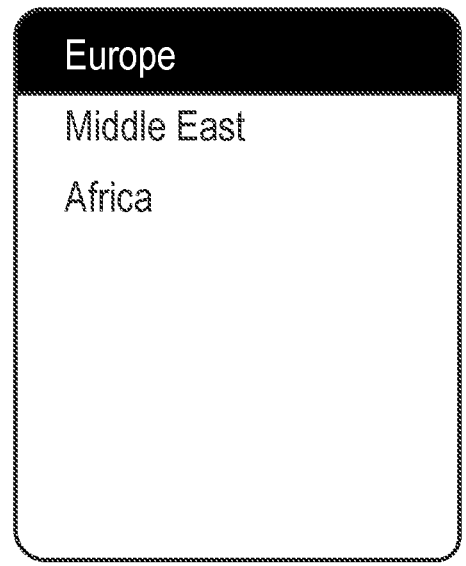
Figure 7P:
Figure 7Q:

As illustrated in FIG. 7I, in preferred embodiments a screen is displayed that enables the user to rescan zone 2 or proceed to the next step. This screen and associated buttons preferably are displayed and operate similarly to what was described in connection with FIGS. 7F and 7G.

As illustrated in FIG. 7J, in preferred embodiments a scan zone 3 screen is displayed. Preferably an indicator to start a zone 3 scan is displayed proximal to one of buttons 9 (e.g., lower center button 9), and the start of the scan is initiated by pressing of the appropriate button 9. In preferred embodiments, as illustrated a graphic is displayed that guides the user to the approximate location of the zone 3 scan.

As illustrated in FIG. 7K, in preferred embodiments a screen is displayed that enables the user to rescan zone 3 or proceed to the next step. This screen and associated buttons preferably are displayed and operate similarly to what was described in connection with FIGS. 7F and 7G.

As illustrated in FIG. 7L, in preferred embodiments a screen is displayed that enables the user to start over the scanning process (in alternative preferred embodiments the start over process goes back to the initiate calibration step or alternatively to the scan zone 1 step) or to proceed to the next step. Preferably the start over and next indicators are displayed proximal to corresponding one of buttons 9 (e.g., lower left and right buttons 9), and the start over or progression to the next step is selected by pressing of the appropriate button 9.

FIG. 7M is similar to FIG. 7L but in FIG. 7L the start over indicator is highlighted, while in FIG. 7M the next indicator is highlighted. In preferred embodiments, once a selection is highlighted, activation of the selected action is initiated by a predetermined one of buttons 9 (e.g., lower center button 9).

As illustrated in FIG. 7N, in preferred embodiments a first product selection screen is displayed such as is illustrated. Preferably this type of product selection screen enables, for example, the user (such as a beauty advisor) to select a product type for selection or matching based on the spectrophotometric data (or data calculated or otherwise determined therefrom) obtained in previous steps (product selection or matching is described in greater detail elsewhere herein). The exemplary screen of FIG. 7N illustrates a serum-type product of LANCÔME (e.g., DreamTone serum; DreamTone is a trademark of LANCÔME) on the left side, preferably with a graphic of a product bottle or other container or identifier for the serum-type product. The exemplary screen of FIG. 7N illustrates a serum-type product of LANCÔME (e.g., DreamTone serum; DreamTone is a trademark of LANCÔME) on the left side, preferably with a graphic of a product bottle or other container or identifier for the serum-type product. The exemplary screen of FIG. 7N further illustrates a foundation-type product of LANCÔME (e.g., Teint Miracle foundation; Teint Miracle is a trademark of LANCÔME) on the right side, preferably with a graphic of a product bottle or other container or identifier for the foundation-type product. In accordance with preferred embodiments, spectrophotometric data obtained in previous steps may be used to select a target or matching product of a first product type in accordance with a first prediction algorithm, and while such spectrophotometric data may be used to select a target or matching products of a second product type, different from the first product type (e.g., serum v. foundation), in accordance with a second prediction algorithm. Such product line and prediction algorithm may be intuitively and easily selected with graphic image guidance. As will be appreciated by those of skill in the art based on the description herein, such prediction algorithms may be optimized based on the particular characteristics of the product line and product line type.

As illustrated in FIGS. 7O and 7Q, in preferred embodiments a product type screen is displayed after selection by a user (e.g., beauty advisor). FIG. 7N is similar to FIG. 7P but in FIG. 7N the serum-type product indicator is highlighted, while in FIG. 7P the foundation-type product indicator is highlighted. In preferred embodiments, once a selection is highlighted, activation of the selected action is initiated by a predetermined one of buttons 9 (e.g., lower center button 9).

Referring again to FIG. 7Q, a first foundation-type produce (e.g., Teint Miracle foundation products) is indicated preferably by way of a graphic (exemplary product bottle shown), and an indicator also is provided that shows that the user may also step through other foundation-type products. In FIG. 7R, after pushing a scroll type button, a second foundation-type product (e.g., Teint Idole Ultra; Teint Idole Ultra is a trademark of LANCÔME) is indicated preferably by way of a graphic (exemplary product bottle shown), and one or a plurality of indicators also are provided that shows that the user may step in one or two directions to other foundation-type products (one direction scrolling and two direction scrolling are both within the scope of the present invention). In FIG. 7T, after pushing a scroll type button, a third foundation-type product (e.g., Teint Visionnaire; Teint Visionnaire is a trademark of LANCÔME) is indicated preferably by way of a graphic (exemplary product bottle shown). In preferred embodiments, once a foundation-type selection is selected, activation of a selection is initiated by a predetermined one of buttons 9 (e.g., lower center button 9), and a foundation-type product is selected (see, e.g., FIG. 7S).

As illustrated in FIG. 7S, a foundation-type product may be selected, which either initiates a selection or matching algorithm as described elsewhere herein or initiates the output of a selection or matching algorithm as described elsewhere herein. In preferred embodiments the selection or matching algorithm is initiated automatically for some or all of the product types and lines so that the results may be displayed more promptly after selection of the product line. In other embodiments, the algorithm is initiated after the product type and specific product line is selected.

As illustrated in FIG. 7U, in preferred embodiments a selected or matching product is displayed, providing a preferably graphic and alpha numeric display of the selection or match. In FIG. 7U, Teint Visionnaire foundation is the selected product line, and 220 Buff C is the particular foundation product that was determined to be the best or optimum selection or match. It should be understood that best or optimum selection or match may indicate a predicted visual match or a product selection that is predicted to a desired selection based on the end result that the product is to achieve. Also as indicated in FIG. 7 U, an indicator preferably is provided such that the user may edit via button push the foundation selection or match, or alternatively may confirm the selection via button push (a confirming selection indicator is shown in FIG. 7U). If the selection or match is confirmed (such as by the beauty or advisor or the end customer applying the foundation and confirming acceptable results), a screen such as is illustrated in FIG. 7W preferably is displayed, which confirms the selection graphically and provides an indicator that a selection may be made to start a new scan with a button push (such as with a new customer, and in such event the sequence may start again at the calibration step or the scan start step, etc).

If the user selects via button push to edit the foundation selection, a screen such as is illustrated in FIG. 7V preferably is displayed. While other alternatives are within the scope of the present invention, FIG. 7V provides an indication of the instrument provided selection via check mark, and the current selection by shading. As illustrated in FIGS. 7X and 7Y, using button pushes (e.g., left/right lower buttons 9) a scrolling through the products of the selected product line may be obtained. In preferred embodiments, the products of the product line are desirably sorted or ordered by optical characteristics (such as value, or by value and hue, etc.) the scrolling steps through the products in a desired and predetermined order. A button push (e.g., center lower button 9) may be used for the user to enter the alternative selection, which leads to the highlighted selection being displayed as in FIG. 7Z (which is similar to FIG. 7W, as previously described). FIGS. 7W and 7Z provide an indication of the selected product and the option to start a new scan (which may lead to the display illustrated in FIG. 7AA, or the calibration screen of FIG. 7B, etc.).

Referring now to FIG. 7BB through FIG. 7EE, exemplary screens are illustrated for connection of the instrument to a companion tablet application and WiFi network. As will be understood from the previous description, buttons 9 may be used to scroll (e.g., left/right lower buttons 9 for up/down, etc.) and make selections (e.g., center lower button 9 for selection). Connection to companion devices (e.g., tablet, computer, smartphone, point of sale terminal, kiosk, etc.) may be made via screens such as in FIGS. 7BB and 7CC. Selection of connection to a WiFi network may be made via screens such as in FIGS. 7DD and 7EE. FIG. 7FF illustrates selection of a network from a displayed list of detected networks (network detection may be made a WiFi module as included in preferred embodiments), and FIG. 7GG illustrates password entry for network security (as one example, alpha numeric characters may be displayed, scrolled and selected via buttons 9, as will be understood from description elsewhere herein). Fig. HH illustrates an exemplary screen indicating to the user that the instrument is in the process of connecting to the WiFi network. Fig. II illustrates an exemplary screen indicating to the user that the instrument is connected to the selected network. Alternates to such screens for connection to companion devices and WiFi networks are within the scope of the present invention.

Figs. JJ through MM will be understood as providing in preferred embodiments exemplary status icons, such as for battery level and charging status (such as with animation of the battery charge level), connection status for a companion device (such as a tablet or smartphone), and connection status to a WiFi network. Such status icons are within the scope of the present invention.

Figs. NN through QQ will be understood as providing in preferred embodiments exemplary screens for selecting location information, such as geographic region (FIG. 7NN), subregions (FIG. 7OO), and countries (FIG. 7PP). In addition, FIG. 7QQ illustrates setting of a country profile. As will be understood from other description herein, buttons 9 desirably enable the scrolling and selection of such geographic information. Other location information, such as cities, store names, location within stores, etc., also are within the scope of the present invention.

Preferably, and in response to user operation via the exemplary displayed screens, spectrophotometric data is obtained and stored in the instrument, as well as tristimulus color values such as $L^*, a^*, b^*,$ and $L^*, C^*, h^*$, etc. Data indicative of the instrument selection via a selection/matching algorithm such as described elsewhere herein, and in cases where a selection edit has been made by a user as described above the edited selection, data indicative of the edited selection also are preferably stored in the instrument. In preferred embodiments, the instrument has a persistent or intermittent network connection by which data from the instrument may be connected to a centralized resource, such as a web-connected database. By way of data connection to a centralized web or network resource, which may be made directly via an HTML service provided in the instrument (e.g., functions included within the configuration of FPGA 34 of FIG. 3 preferably includes an HTML service, etc.) or via an intermediate computer, tablet or smartphone, such data preferably is transmitted via the data connection to the centralized resource. Within the scope of the present invention are wireless data connections, such as Bluetooth or WiFi connection, and/or wired data connections, such as USB or LAN.

In accordance with embodiments of the present invention, data is stored within the centralized resource, and in addition subsequent data processing is performed via the centralized resource, which may occur directly with the centralized or remotely via one or more computers or servers having access to data stored in or via the centralized resource. Such processing, may for example, provide updates to improved selection or matching algorithms and/or tables or other data structures used in the instrument to carry out a prediction algorithm as described elsewhere herein. Also within the scope of the present invention are transmittal to the centralized resource of some or all of the following: information that identifies the instrument (such as via MAC address or other identifier such as device serial number); information that indicates the geographic location of the instrument, such as store or other commercial location of the instrument; information indicative of the software ore firmware version of, for example, the FPGA configuration or other software in the case of non-FPGA embodiments; normalization or calibration data such as obtained via the calibration process initiated via FIG. 7B; information indicative of the normalization or calibration reference used in the instrument, which may be initial normalization data or an identifier for the initial normalization reference; and date and time stamps for the measurement, which may be provided via a real time clock function as a separate module or in the WiFi module, or via a clock that is updated from time to time by network connection (in other embodiments, the time stamp is simply the date and time received by the centralized resource). Such data generation and/or storage in the instrument, and transmission to one or more remote and/or centralized resources (e.g., database, cloud-based data storage or web services) are within the scope of the present invention. In addition, as described elsewhere herein, updates to the configuration data, software, prediction algorithms, prediction data structures also are within the scope of the present invention, and one or more centralized resources desirably provide such update data to instruments as contemplated herein (this may be the same or different centralized resources, but in any event such updates are provided down to the instruments based on data previously transmitted by the instrument up to the centralized resource).

Although the invention has been described in conjunction with specific preferred and other embodiments, it is evident that many substitutions, alternatives and variations will be apparent to those skilled in the art in light of the foregoing description. Accordingly, the invention is intended to embrace all of the alternatives and variations that fall within the spirit and scope of the appended claims. For example, it should be understood that, in accordance with the various alternative embodiments described herein, various systems, and uses and methods based on such systems, may be obtained. The various refinements and alternative and additional features also described may be combined to provide additional advantageous combinations and the like in accordance with the present invention. Also as will be understood by those skilled in the art based on the foregoing description, various aspects of the preferred embodiments may be used in various subcombinations to achieve at least certain of the benefits and attributes described herein, and such subcombinations also are within the scope of the present invention. All such refinements, enhancements and further uses of the present invention are within the scope of the present invention.

The invention claimed is:

1. A single-beam spectrophotometer apparatus for measuring optical properties of an object, comprising:
    a spectrometer and a light source under control of a processing circuit;
    an optical cavity into which illumination from the light source is provided, wherein the cavity has an opening for illuminating a portion of the object;
    three reference reflectance standards of differing spectral reflectance properties, wherein each of the three reference reflectance standards has a surface for positioning such that the opening illuminates in turn a respective one of the three reference reflectance standards;
    a normalization reference standard having a surface for positioning such that the opening illuminates the normalization reference standard;
    wherein the spectrometer is configured to receive light from the object and to generate spectral data based on light received from the object;
    wherein the spectrometer is configured to receive light from each of the three reference reflectance standards and to generate spectral data based on the light received from the three reference reflectance standards;
    wherein the spectrometer is configured to receive light from the normalization reference standard and to generate spectral data based on the light received from the normalization reference standard;
    a storage circuit coupled to the processing circuit;
    wherein a measurement is made of each of the three reference reflectance standards, wherein based on the measurement of the three reference reflectance standards the spectrometer provides spectral data to the processing circuit, wherein the processing circuit determines three parameters for calibration of the apparatus that reduce sample substitution error, wherein data indicative of the three parameters for calibration of the apparatus are stored in the storage circuit;
    wherein a first measurement is made of the normalization reference standard, wherein based on the first measurement of the normalization reference standard the spectrometer provides spectral data to the processing circuit, wherein the processing circuit determines data indicative of properties of the illumination from the light source at a time of the first measurement, wherein the data indicative of the properties of the illumination from the light source at the time of the first measurement are stored in the storage circuit;
    wherein a second measurement is made of the normalization reference standard, wherein based on the second measurement of the normalization reference standard the spectrometer provides spectral data to the processing circuit, wherein the processing circuit determines data indicative of properties of the illumination from the light source at a time of the second measurement, wherein the data indicative of the properties of the illumination from the light source at the time of the second measurement are stored in the storage circuit;
    wherein a measurement is made of the object, wherein based on the measurement of the object the spectrometer provides spectral data to the processing circuit, wherein the processing circuit determines output spectral data indicative of spectral properties of the object based on (1) the spectral data from the measurement of the object, (2) the data indicative of the three parameters for calibration, (3) the data indicative of the properties of the illumination from the light source at the time of the first measurement and (4) the data indicative of the properties of the illumination from the light source at the time of the second measurement, wherein sample substitution error is reduced and wherein changes in illumination of the light source are compensated.

2. The apparatus of 1, wherein the cavity is approximately hemispherical.

3. The apparatus of 1, wherein the cavity is approximately spherical.

4. The apparatus of 1, wherein sample illumination is provided by one or more light emitting diodes.

5. The apparatus of 1, wherein sample illumination is provided by one or more incandescent lights.

6. The apparatus of 1, wherein a fourth reflectance reference standard is measured, wherein based on the measurement of the fourth reference reflectance standards the spectrometer provides spectral data to the processing circuit, wherein the processing circuit determines data indicative of sample edge loss of the object.

7. The apparatus of 1, wherein the three reflectance reference standards comprise reflectance standards having differing levels of gray.

* * * * *